(12) United States Patent
Noda et al.

(10) Patent No.: US 7,833,209 B2
(45) Date of Patent: *Nov. 16, 2010

(54) ABSORBENT ARTICLE

(75) Inventors: Yuki Noda, Kagawa (JP); Kenichiro Kuroda, Kagawa (JP); Kumiko Nishikawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 552 days.

This patent is subject to a terminal disclaimer.

(21) Appl. No.: 11/757,130

(22) Filed: Jun. 1, 2007

(65) Prior Publication Data

US 2007/0282288 A1 Dec. 6, 2007

(30) Foreign Application Priority Data

Jun. 2, 2006 (JP) ............................. 2006-155113
May 24, 2007 (JP) ............................. 2007-137764

(51) Int. Cl.
*A61F 13/15* (2006.01)
*A61F 13/20* (2006.01)
(52) U.S. Cl. ............................. 604/385.03; 604/385.16
(58) Field of Classification Search ............ 604/385.01, 604/385.14, 385.16, 385.03, 386–391
See application file for complete search history.

(56) References Cited

U.S. PATENT DOCUMENTS 5,611,790 A * 3/1997 Osborn et al. ................ 604/391

FOREIGN PATENT DOCUMENTS

| JP | 332094 Y1 | 2/1958 |
| JP | S53-121799 | 9/1978 |
| JP | 03-101933 U | 10/1991 |
| JP | 11-099179 A | 4/1999 |

(Continued)

OTHER PUBLICATIONS

International Search Report of PCT/JP2007/061206 filed Aug. 7, 2007.

(Continued)

*Primary Examiner*—Michele Kidwell
(74) *Attorney, Agent, or Firm*—Lowe, Hauptman, Ham & Berner, LLP

(57) ABSTRACT

An elongated absorbent article including: an absorbent article body having at least: (a) a top sheet part which is at least partially liquid permeable and arranged on a first side in a thickness direction of the absorbent article; and (b) a liquid retainable absorber part arranged on a second side in the thickness direction of the absorbent article body; a cover member arranged on the second side in the thickness direction of the absorbent article body; an extensible belt-shaped member disposed between the absorbent article body and the cover member, a first end portion of the belt-shaped member being connected to the absorbent article body; an engaging part arranged at a second end portion of the belt-shaped member on a surface thereof on which the cover member is disposed; a peelable sheet arranged along a surface of the engaging part; and a fixing part for connecting and fixing the peelable sheet to the cover member; the fixing part being formed so that an end portion thereof in a direction of elongation of the belt-shaped member is arranged at either one of a position corresponding to an end portion of the engaging part in the direction of elongation, and a position more towards the direction of elongation. This improves the adhesion between the wearer's excretory part and the absorbent article, thereby preventing the leakage of excrement such as menstrual blood.

15 Claims, 30 Drawing Sheets

FOREIGN PATENT DOCUMENTS

| | | |
|---|---|---|
| JP | 2000-083992 A | 3/2000 |
| JP | 2003-038563 A | 2/2003 |
| JP | 2003-38574 A | 2/2003 |
| JP | 2003-310659 A | 11/2003 |

OTHER PUBLICATIONS

International Search Report for PCT/JP2007/060541 issued Aug. 7, 2007.

* cited by examiner

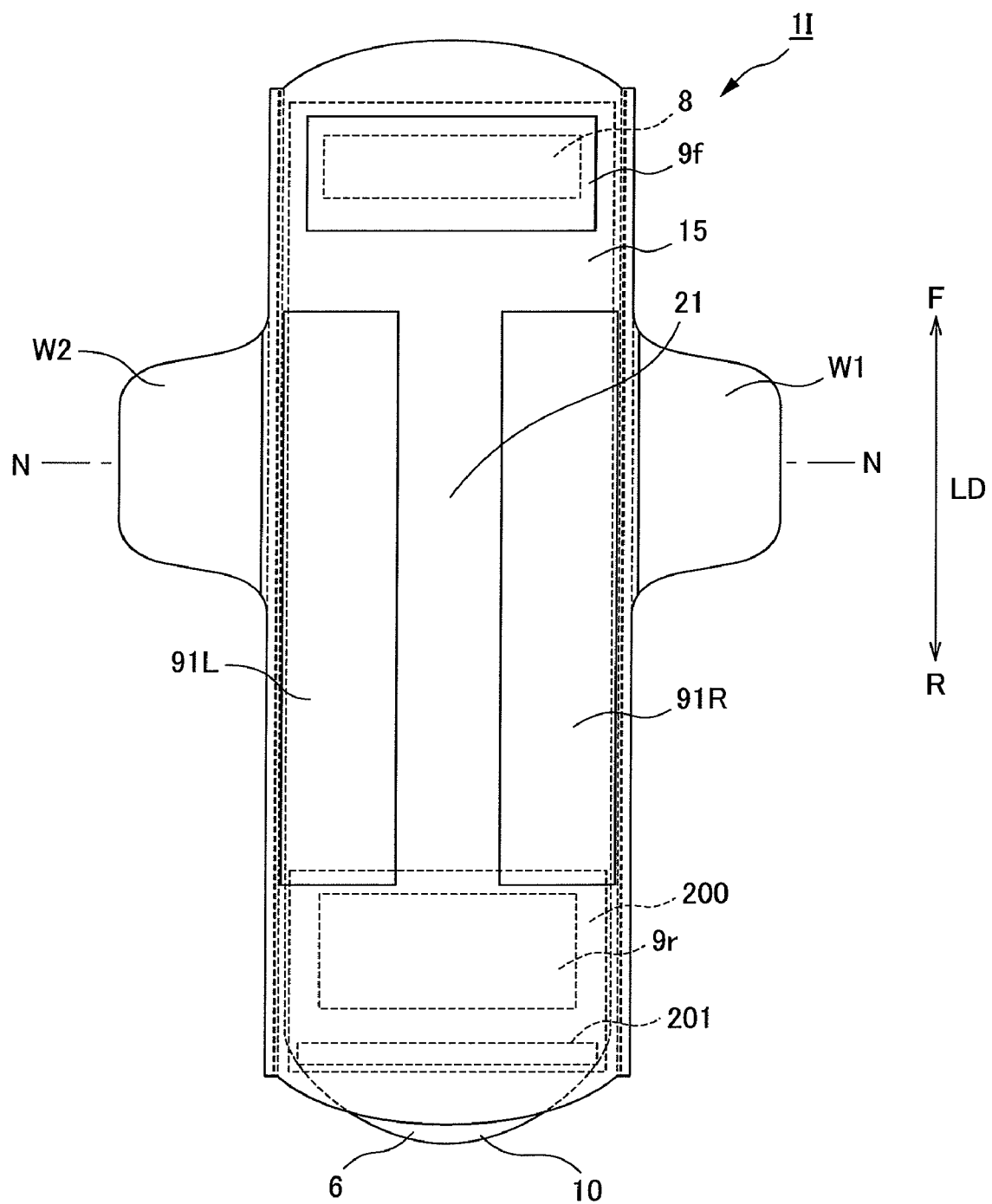

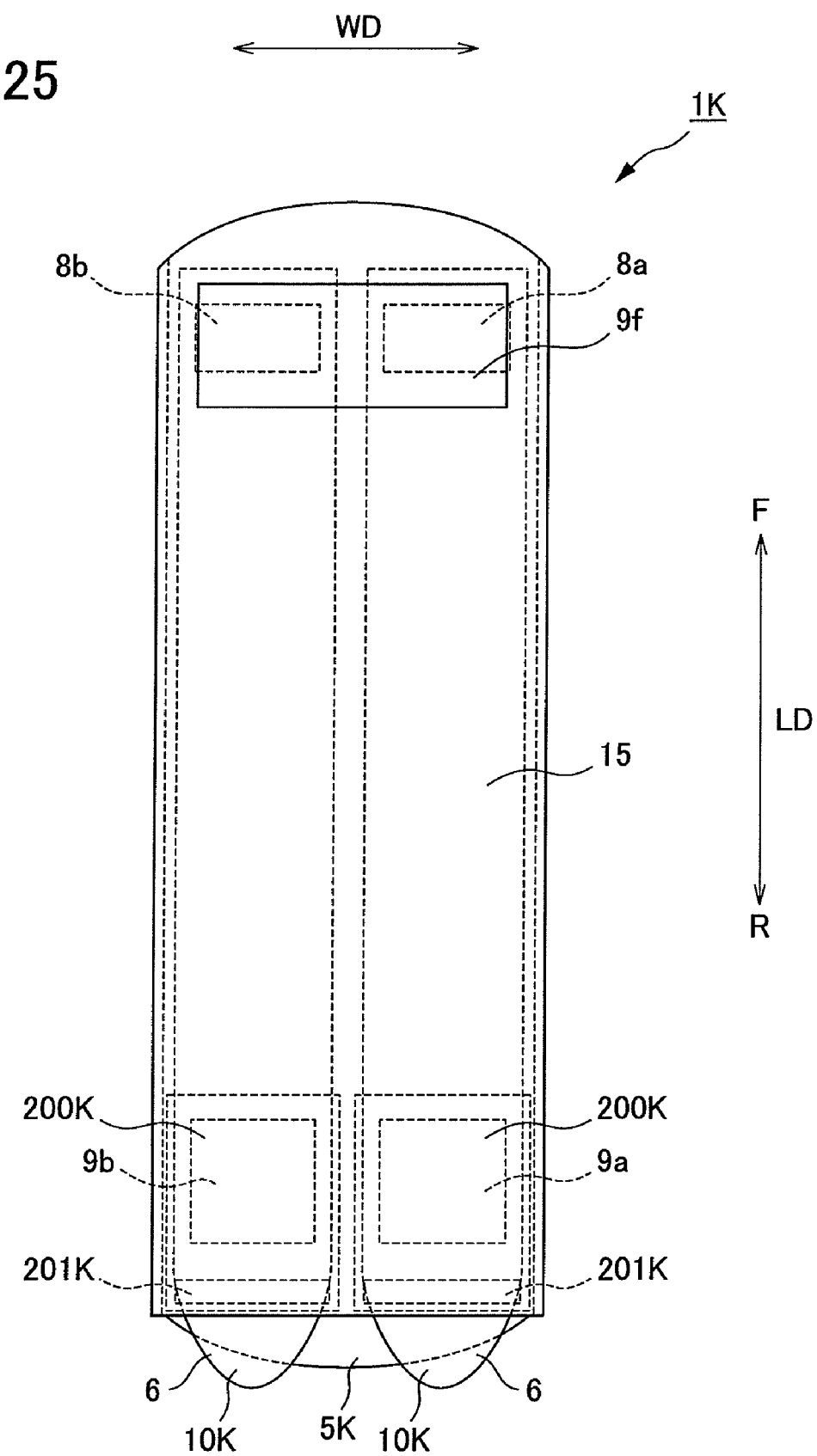

ABSORBENT ARTICLE

This application is based on and claims the benefit of priority from Japanese Patent Application No. 2006-155113, filed on Jun. 2, 2006, and Japanese Patent Application No. 2007-137764, filed on May 24, 2007, the content of which is incorporated herein by reference.

BACKGROUND OF THE INVENTION

1. Field of the Invention

The present invention relates to an absorbent article.

2. Related Art

Sanitary napkins, panty liners, urine-absorbing pads, and the like have conventionally been used as an absorbent article for absorbing excrement such as menstrual blood. These absorbent articles have an absorber that forms an absorption layer by absorbing and holding menstrual blood or the like, a liquid permeable top sheet that covers the surface on a skin contacting surface of the absorber, and a liquid impermeable back sheet that covers the back positioned on the clothing side of the absorber. For example, these absorbent articles can be adhered to the internal surface of a groin piece of underwear.

In order to catch the excrement such as menstrual blood, it is desired that the abovementioned absorbent articles be used in a state where the absorption layer having the absorber is in contact with the excretory part of a wearer. However, since the absorbent articles are by nature adapted for use in the state where these are attached to underwear or the like, both are susceptible to relative dislocation between the underwear and the excretory part. If there is a space between the excretory part and the absorbent article, the excrement dropped on the top sheet may effuse along the top sheet toward the sides and the buttocks, resulting in soiling of the underwear and clothing.

Related to this, for example, Japanese Unexamined Utility Model Application No. H3-101933 (hereinafter referred to as "patent document 1") discloses an absorbent article having improved contact of the absorbent article to the human body during the time underwear is worn. Specifically, flexible flaps are formed on both ends in the longitudinal direction of the absorbent article, and retainers provided at the flaps can be adhered to the underwear.

On the other hand, Japanese Unexamined Patent Application No. H11-99179 (hereinafter referred to as "patent document 2") discloses an absorbent article having improved contact of the absorbent article to the human body during the time underwear is worn. Specifically, a flexible elastic member can be extended from the edge part of a sanitary napkin, and an adhesive region is formed on a contact surface with the underwear located at the part so extended. The adhesive region is then adhered to the underwear or the like.

More specifically, each of the absorbent articles as disclosed in patent document 1 and patent document 2 is provided with the elastic members on both ends of the absorbent article in the longitudinal direction, and adapted to improve contact by pulling the absorbent article toward the excretory part of the wearer by the elastic force generated in the elastic members.

SUMMARY OF THE INVENTION

However, the absorbent articles disclosed in patent document 1 and patent document 2 have the construction of pulling the absorbent article back and forth by the elastic force of the elastic members provided on both ends of the absorbent article. Therefore, sufficient force might not be obtained to contact the absorbent article with the excretory part. When the absorbent article is being attached, the retainer and an adhesive region may be adhered to somewhere other than a desired position on the underwear or the like. Consequently, there is difficulty in the attachment operation.

The present invention has been made in view of the foregoing problems, and aims at providing an absorbent article that improves the contact between the excretory part of a wearer and the absorbent article by incorporating a belt-shaped member having a predetermined engaging part in the absorbent article. The invention also aims at providing an absorbent article having an improvement in operability at the time of the attachment, with the arrangement that the engaging part is covered with a peelable sheet, and the peelable sheet can be separated when the belt-shaped member is stretched.

To this end, the present inventors have made the present invention based on the discovery that an absorbent article body can contact the excretory part or the like by engaging an engaging part to an underwear, etc. with the whole of the absorbent article body lifted. The engaging part is formed so that it can be easily exposable from the absorbent article when attaching the absorbent article and is disposed on one end of a belt-shaped member, the other end of which is connected to a non-skin contact surface of the absorbent article body. Specifically, the present invention provides the following absorbent articles.

In a first aspect of the present invention, an elongated absorbent article includes: an absorbent article body having at least: (a) a top sheet part which is at least partially liquid permeable and arranged on a first side in a thickness direction of the absorbent article, and (b) a liquid retainable absorber part arranged on a second side in the thickness direction of the absorbent article body; a cover member arranged on the second side in the thickness direction of the absorbent article body; an extensible belt-shaped member disposed between the absorbent article body and the cover member, a first end portion of the belt-shaped member being connected to the absorbent article body; an engaging part arranged at a second end portion of the belt-shaped member on a surface thereof on which the cover member is disposed; a peelable sheet arranged along a surface of the engaging part; and a fixing part for connecting and fixing the peelable sheet to the cover member, the fixing part being formed so that an end portion thereof in a direction of elongation of the belt-shaped member is arranged at either one of a position corresponding to an end portion of the engaging part in the direction of elongation, and a position more towards in the direction of elongation.

In a second aspect of the absorbent article as described in the first aspect of the present invention, the cover part is arranged so as to encase at least a part of the engaging part.

In a third aspect of the absorbent article as described in the first or second aspect of the present invention, at least a part of the belt-shaped member is formed so as to be flexible.

The term "formed so as to be extensible" means, for example, applying a corrugated embossing finish to or forming a predetermined flap in the belt-shaped member. Alternatively, an extensible base material sheet may be used.

In a fourth aspect of the absorbent article as described in any one of the first to third aspects of the present invention, the belt-shaped member has a grip part at the second end portion thereof, the grip part extending from an outer edge portion of the absorbent article body in a longitudinal direction.

In a fifth aspect of the absorbent article as described in the fourth aspect of the present invention, the grip part has a guide element implying the direction of elongation of the belt-shaped member.

In a sixth aspect of the absorbent article as described in the fourth or fifth aspect of the present invention, the second end portion of the belt-shaped member is provided with a predetermined absorbent member.

In a seventh aspect of the absorbent article as described in the sixth aspect of the present invention, the absorbent member is arranged in a region extending from the outer edge portion of the absorbent article body in the longitudinal direction, when the belt-shaped member is in one of an extended state and a elongated state.

In an eighth aspect of the absorbent article as described in the sixth or seventh aspect of the present invention, the belt-shaped member has a liquid impermeable sheet disposed in a region corresponding to the absorbent member on the opposite side of the absorbent article body.

In a ninth aspect of the absorbent article as described in any one of the first to eighth aspects of the present invention, a length of the belt-shaped member in a width direction is at least 30% of a length of the absorbent article body in the width direction.

In a tenth aspect of the absorbent article as described in any one of the first to ninth aspects of the present invention, the belt-shaped member has a belt-shaped base material sheet and an elastic member.

In an eleventh aspect of the absorbent article as described in any one of the first to tenth aspects of the present invention, at least a part of the belt-shaped member has a liquid impermeable material.

As an alternative, the liquid impermeable sheet may be arranged so as to cover the outer edge portion on the other end of the belt-shaped member. This enables soaking through of the absorbed excrement or the like to the outer edge portion of the belt-shaped member to be prevented. As another alternative, the liquid impermeable member may be arranged so as to cover at least a part of both side parts in the region extending from the outer edge portion of the absorbent article body in the longitudinal direction. This prevents the absorbed excrement or the like from soaking through both side portions of the belt-shaped member.

In a twelfth aspect of the absorbent article as described in any one of the first to eleventh aspects of the present invention, at least a part of the cover member is formed of a liquid impermeable material.

In a thirteenth aspect of the absorbent article as described in any one of the first to twelfth aspects of the present invention, at least a part of the cover member is formed so as to be stretchable in a width direction of the belt-shaped member.

In a fourteenth aspect of the present invention, an elongated absorbent article includes: (i) an absorbent article body having at least (a) a top sheet part which is at least partially liquid permeable and arranged on a first side in a thickness direction of the absorbent article, and (b) a liquid retainable absorber part disposed on a second side in the thickness direction of the absorbent article body; (ii) a cover member arranged on the second side in the thickness direction of the absorbent article; (iii) an extensible belt-shaped member disposed between the absorbent article body and the cover member, a substantially central part of the belt-shaped member being connected to the absorbent article body; (iv) an engaging part arranged on both end portions of the belt-shaped member on a surface thereof on which the cover member is disposed; (v) a peelable sheet arranged along a surface of the engaging part; and (vi) a fixing part for connecting and fixing the peelable sheet to the cover member. The fixing part is formed so that an end portion thereof in a direction of elongation of the belt-shaped member is arranged at one of a position corresponding to an end portion of the engaging part in the direction of elongation, and a position more towards the direction of elongation.

In a fifteenth aspect of the present invention, an elongated absorbent article includes: (i) an absorbent article body having at least: (a) a top sheet part which is at least partially liquid permeable and arranged on a first side in a thickness direction of the absorbent article, (b) a liquid impermeable back sheet part arranged on a second side in the thickness direction, and (c) a liquid retainable absorber part disposed between the top sheet part and the back sheet part; (ii) an extensible belt-shaped member disposed between the absorber part and the back sheet part, a first end portion of the belt-shaped member being connected to the absorbent article body; (iii) an engaging part arranged at a second end portion of the belt-shaped member on a surface thereof on which the back sheet part is disposed; (iv) a peelable sheet arranged along a surface of the engaging part; and (v) a fixing part for connecting and fixing the peelable sheet to the cover member. The fixing part is formed so that an end portion thereof in a direction of elongation of the belt-shaped member is arranged at either one of a position corresponding to an end portion of the engaging part in the direction of elongation, and a position more towards in the direction of elongation.

Thus, the present invention can provide an absorbent article with improved adhesion between the excretory part of a wearer and the absorbent article, and also facilitates attachment operation by incorporating a belt-shaped member having a predetermined engaging part in the absorbent article. The invention can also provide an absorbent article having an improvement in operability at the time of attachment, with the arrangement that the engaging part is covered with the peelable sheet, and the peelable sheet is separated when the belt-shaped member is stretched.

BRIEF DESCRIPTION OF THE DRAWINGS

FIG. 23A is a back view of a sanitary napkin according to a ninth embodiment of the present invention.

FIG. 25 is a back view of a sanitary napkin according to an eleventh embodiment of the present invention.

DETAILED DESCRIPTION OF THE INVENTION

Embodiments of the present invention are described below with reference to the accompanying drawings. However, it is to be understood that the embodiments of the present invention are not limited to the following, and the technical scope of the present invention is not limited to these.

Although the absorbent articles according to the present invention are worn on the crotch of the human body in order to absorb menstrual blood, urine, and leukorrhea discharged from the human body, the following embodiments are directed to sanitary napkins, the primary object of which is to absorb menstrual blood discharged from the vaginal opening of females. In the following description, one of two surfaces of the absorbent article, which is directed to the excretory part, is called "skin contact surface", and the other is called "non-skin contact surface", irrespective of whether clothing is in contact with the outside thereof.

Figure 1:
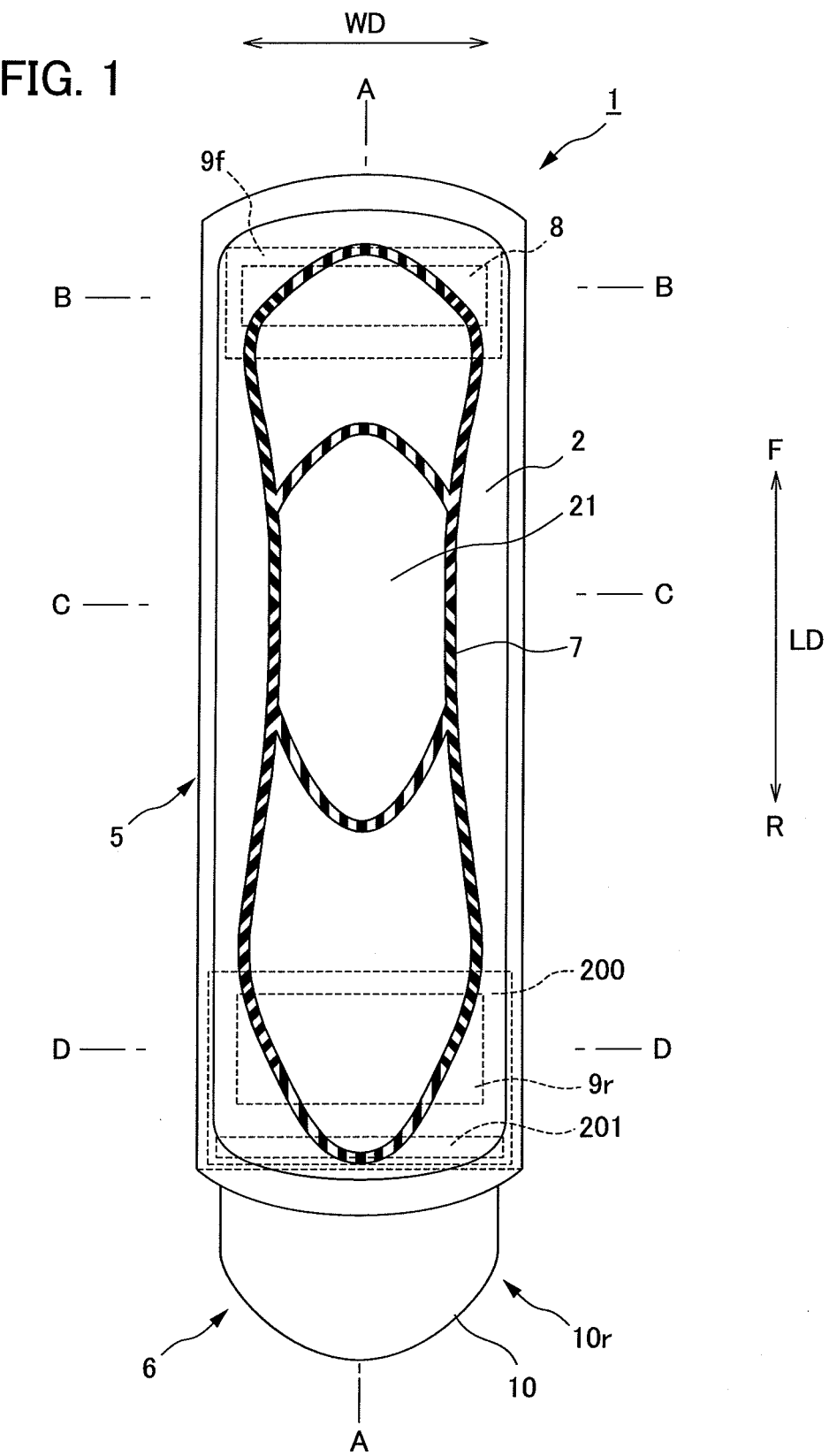
FIG. 1 is a front view of a sanitary napkin according to a first embodiment of the present invention.
Figure 2:
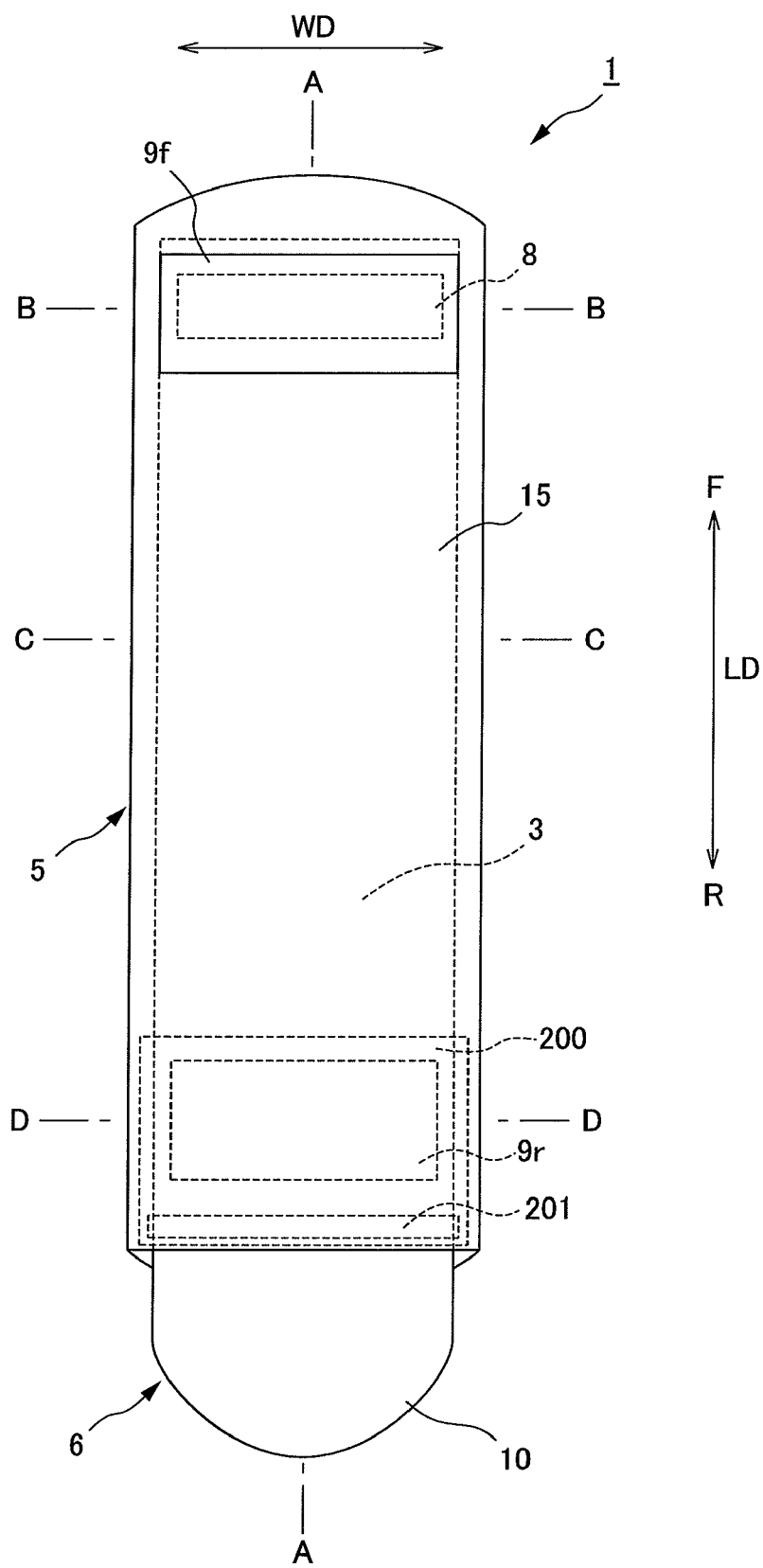
FIG. 2 is a back view of FIG. 1.
Figure 3:
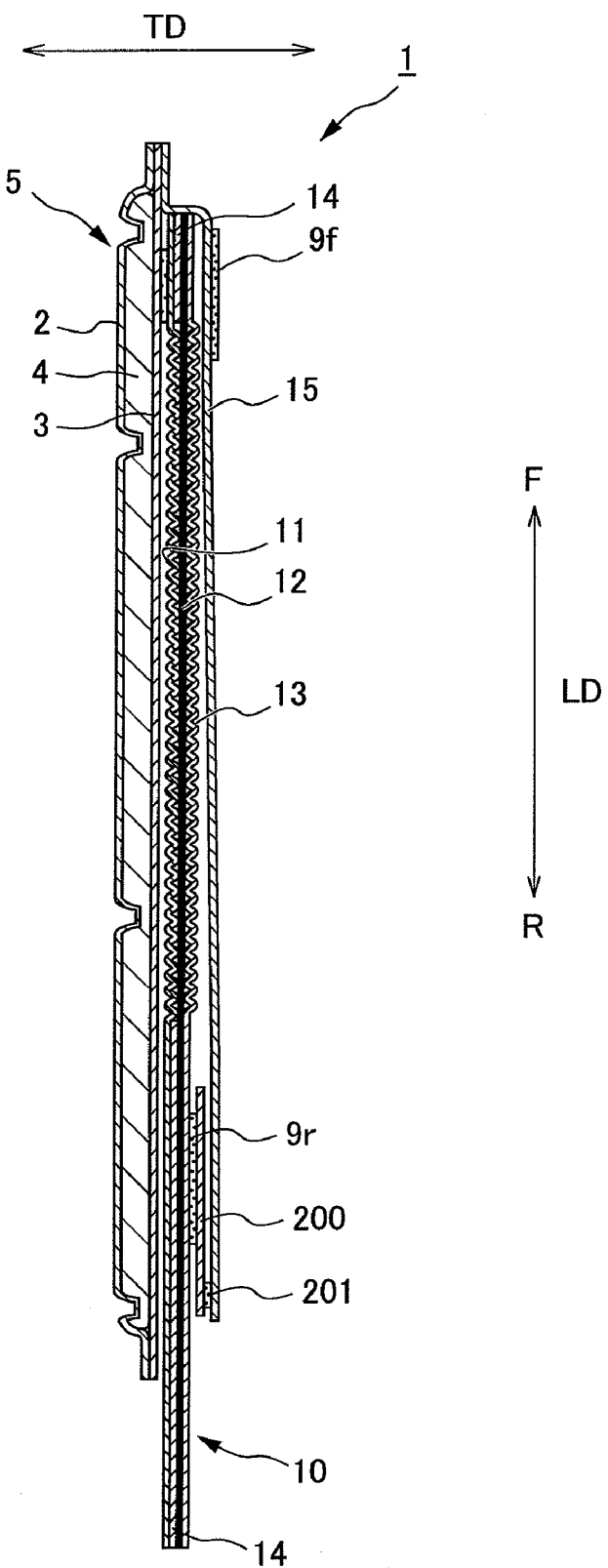
FIG. 3 is a sectional view taken along the line A-A of FIG. 1.
Figure 4A:
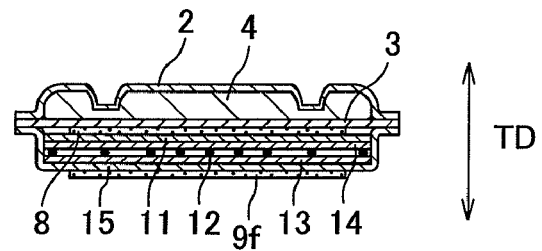
FIG. 4A is a sectional view taken along the line B-B of FIG. 1.
Figure 4B:
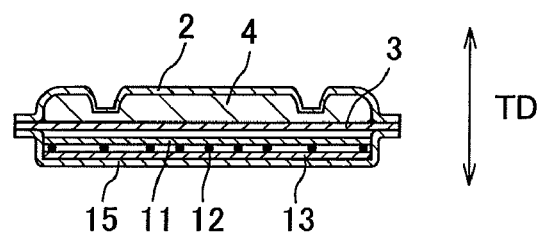
FIG. 4B is a sectional view taken along the line C-C of FIG. 1.
Figure 4C:
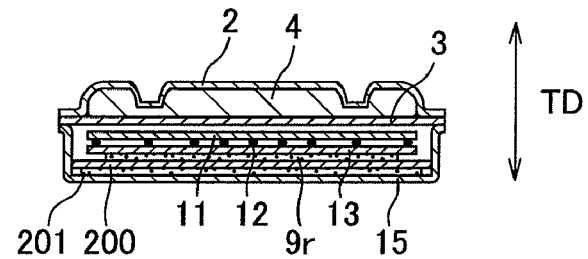
FIG. 4C is a sectional view taken along the line D-D of FIG. 1.
Figure 5:
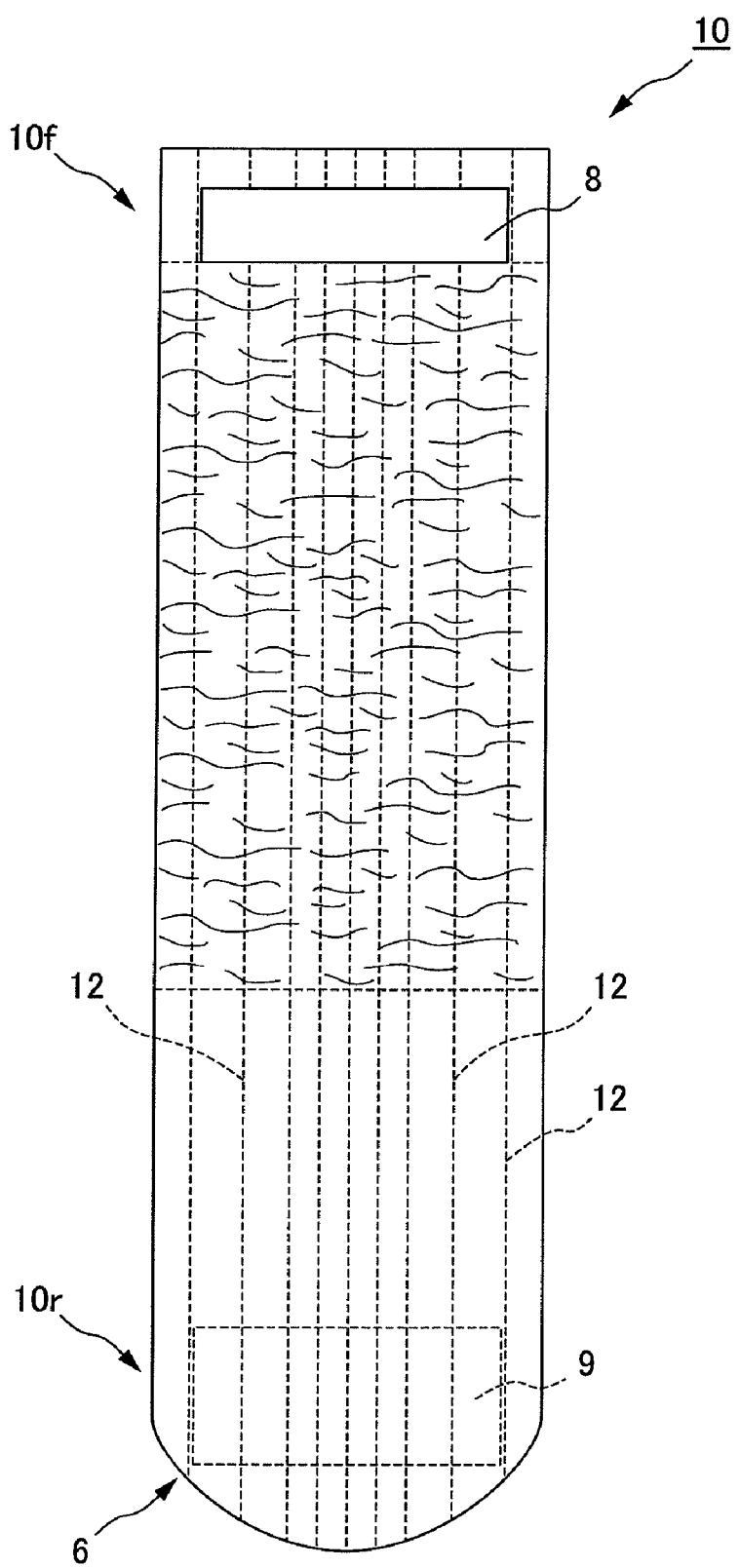
FIG. 5 is a front view of a belt-shaped member according to the first embodiment.
Figure 6:
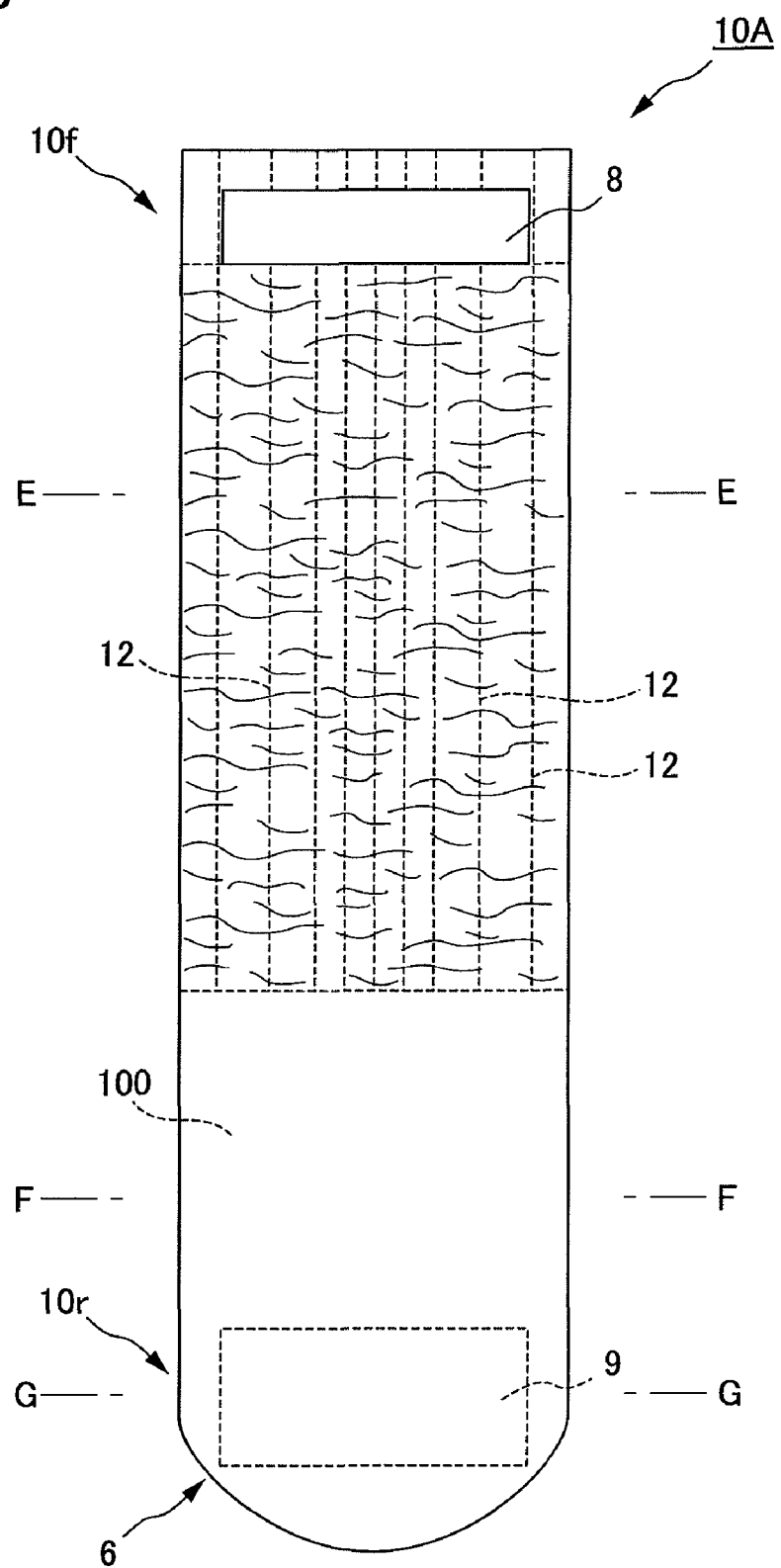
FIG. 6 is a front view illustrating another embodiment of the belt-shaped member.
Figure 7A:
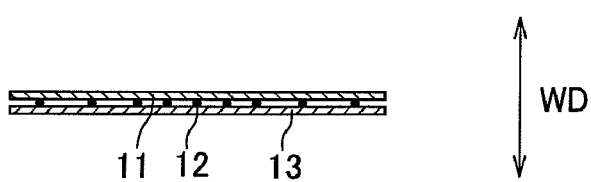
FIG. 7A is a sectional view taken along the line E-E of FIG. 6.
Figure 7B:
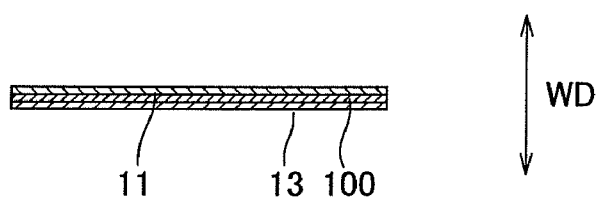
FIG. 7B is a sectional view taken along the line F-F of FIG. 6.
Figure 7C:
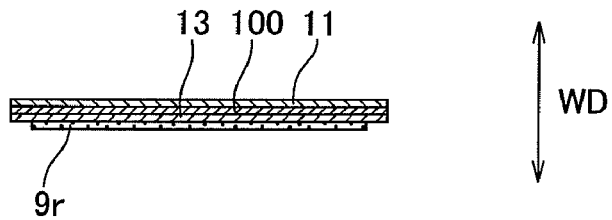
FIG. 7C is a sectional view taken along the line G-G of FIG. 6.
Figure 8:
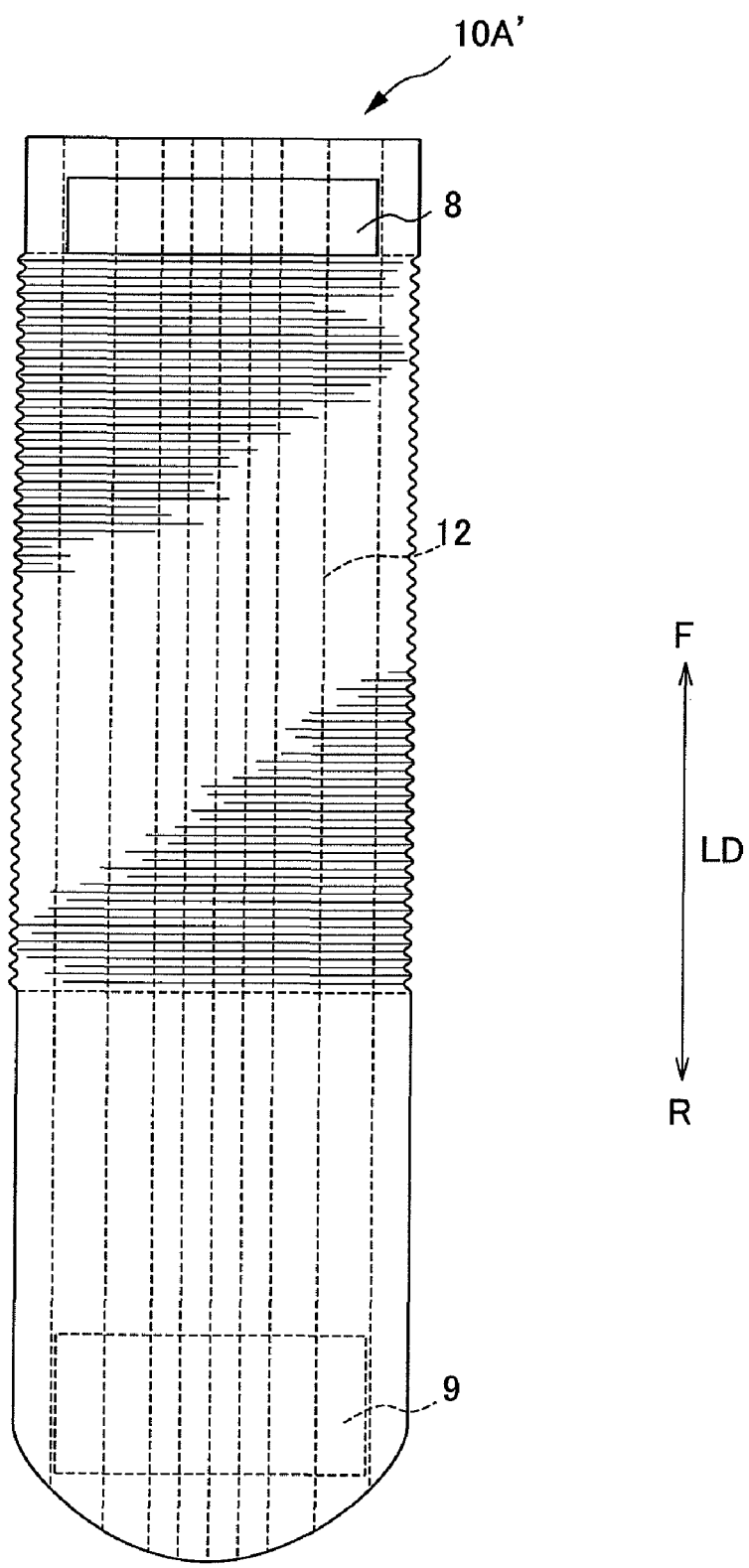
FIG. 8 is a diagram illustrating still another embodiment of the belt-shaped member.
Figure 9A:
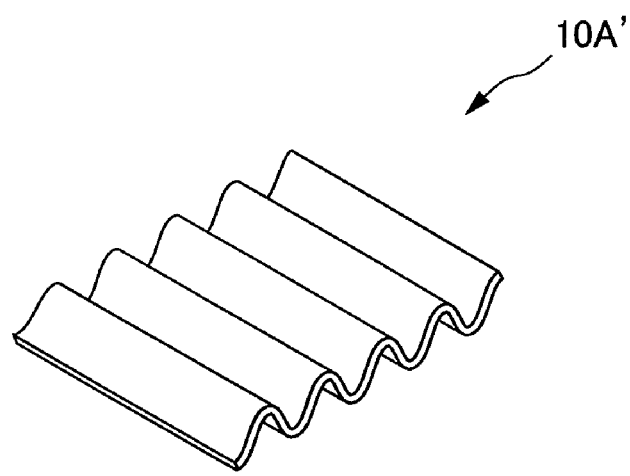
FIG. 9A is a partially enlarged view of FIG. 8.
Figure 9B:
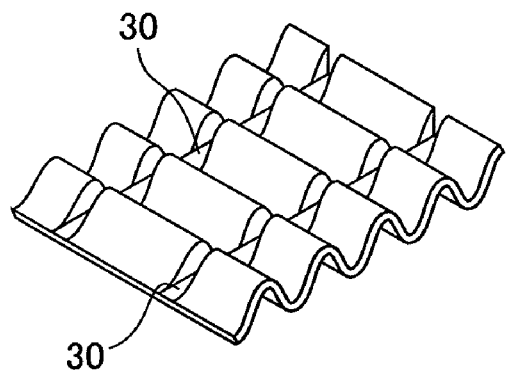
FIG. 9B is a partially enlarged view illustrating a modification of FIG. 9A.
Figure 10:
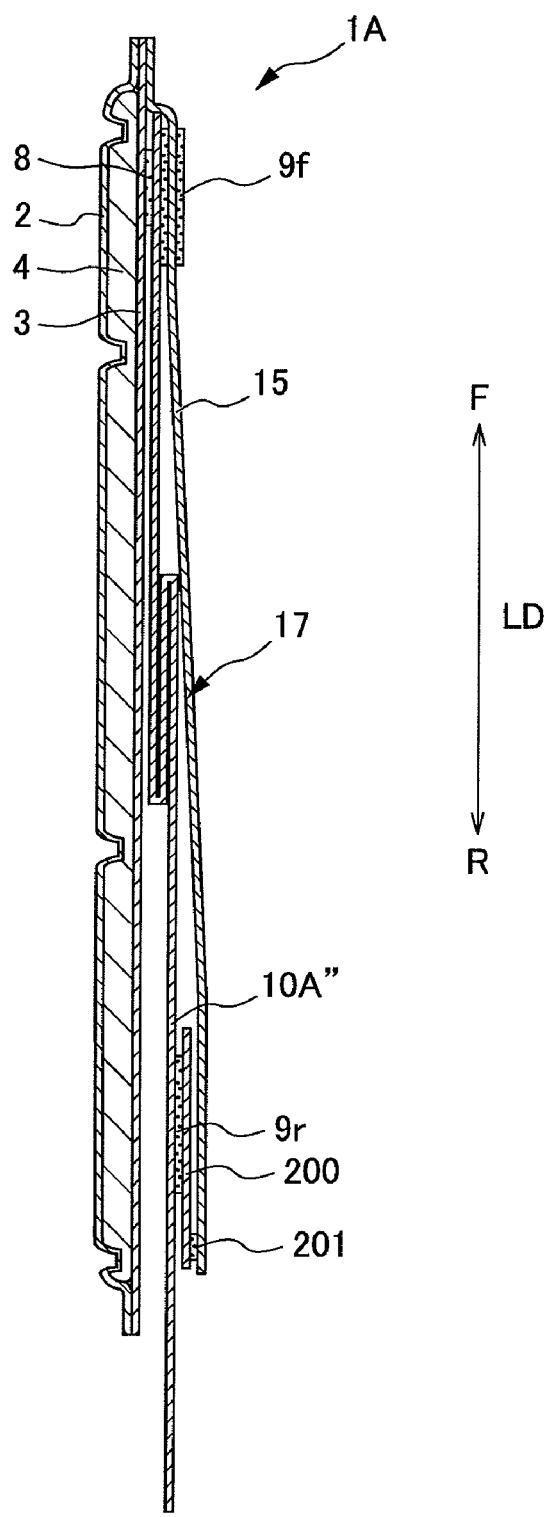
FIG. 10 is a sectional view illustrating another configuration of the sanitary napkin.

FIG. 1 is a front view of a sanitary napkin according to a first embodiment of the present invention. FIG. 2 is a back view of FIG. 1. FIG. 3 is a sectional view taken along the line A-A of FIG. 1. FIG. 4A is a sectional view taken along the line B-B of FIG. 1; FIG. 4B is a sectional view taken along the line C-C of FIG. 1; and FIG. 4C is a sectional view taken along the line D-D of FIG. 1. FIG. 5 is a front view of a belt-shaped member according to the first embodiment. FIG. 6 is a front view illustrating another embodiment of the belt-shaped member. FIG. 7A is a sectional view taken along the line E-E of FIG. 6; FIG. 7B is a sectional view taken along the line F-F of FIG. 6; and FIG. 7C is a sectional view taken along the line G-G of FIG. 6. FIG. 8 is a diagram illustrating still another embodiment of the belt-shaped member. FIG. 9A is a partially enlarged view of FIG. 8; and FIG. 9B is a partially enlarged view illustrating a modification of FIG. 9A. FIG. 10 is a sectional view illustrating other configuration of the sanitary napkin.

Figure 11A:
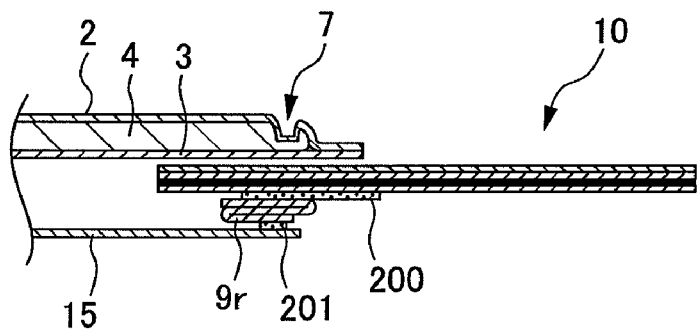
FIGS. 11A and 11B are partial sectional views illustrating the attached state of the sanitary napkin according to the first embodiment.
Figure 11B:
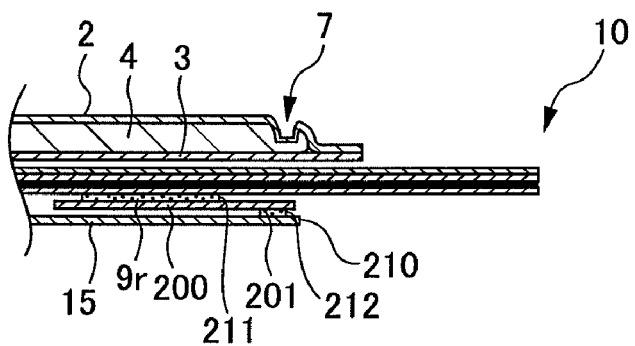
Figure 12A:
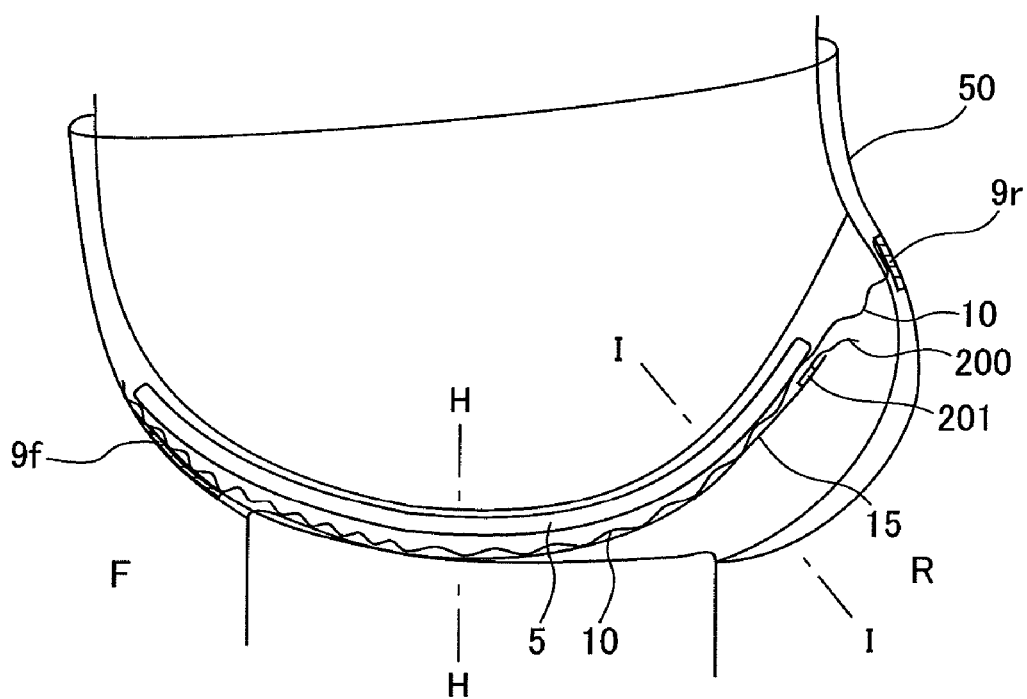
FIG. 12A is a diagram illustrating a state where the sanitary napkin according to the first embodiment is attached.
Figure 12B:
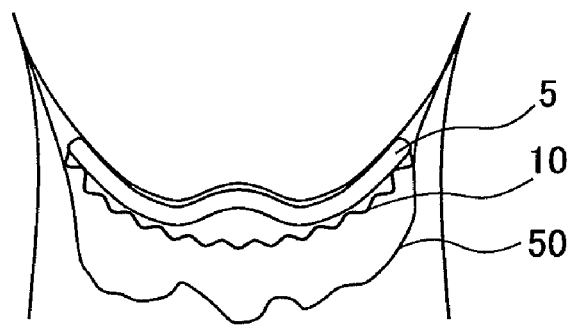
FIG. 12B is a sectional view taken along the line H-H of FIG. 12A.
Figure 12C:
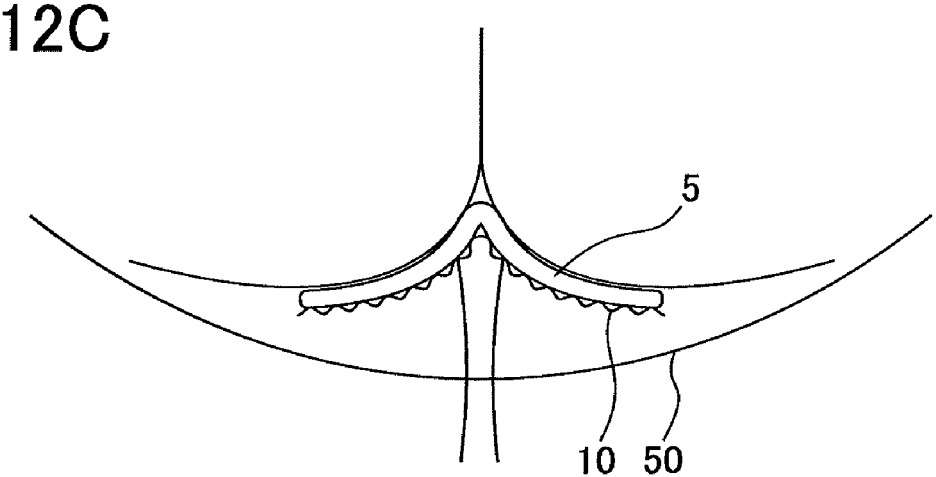
FIG. 12C is a sectional view taken along the line I-I of FIG. 12A.
Figure 13:
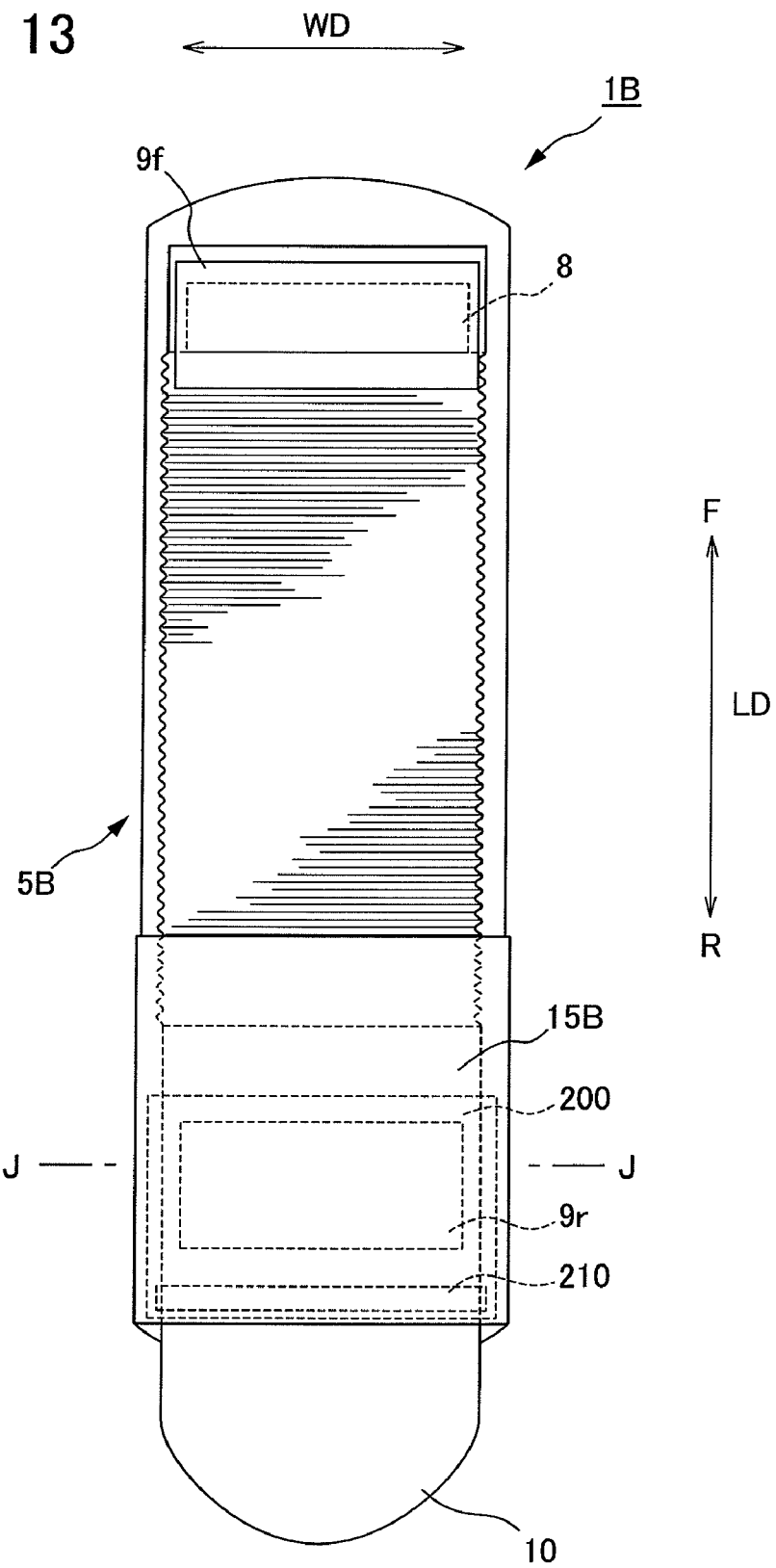
FIG. 13 is a back view of a sanitary napkin according to a second embodiment of the present invention.
Figure 14A:
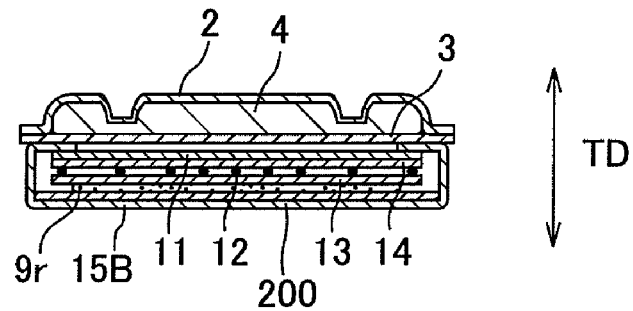
FIG. 14A is a sectional view taken along the line J-J of FIG. 13.
Figure 14B:
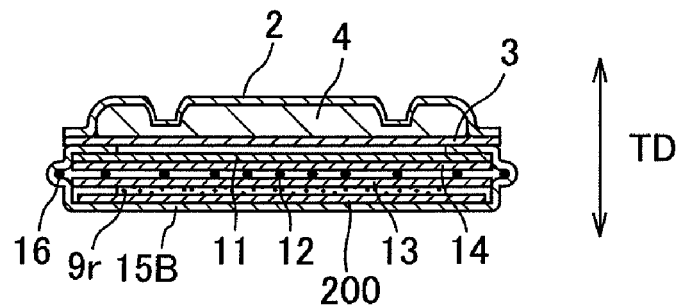
FIG. 14B is a sectional view illustrating another configuration of FIG. 14A.
Figure 15:
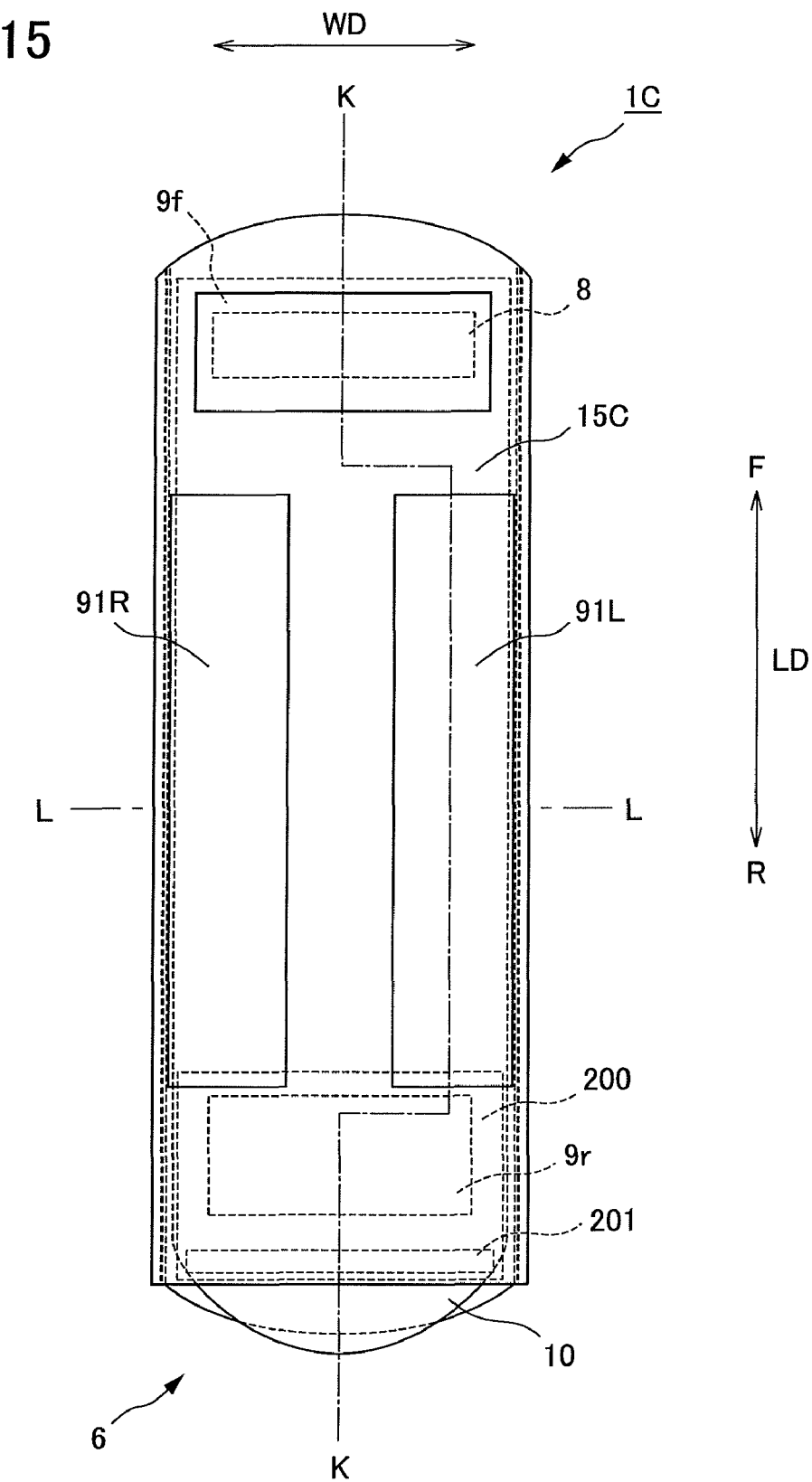
FIG. 15 is a back view of a sanitary napkin according to a third embodiment of the present invention.
Figure 16A:
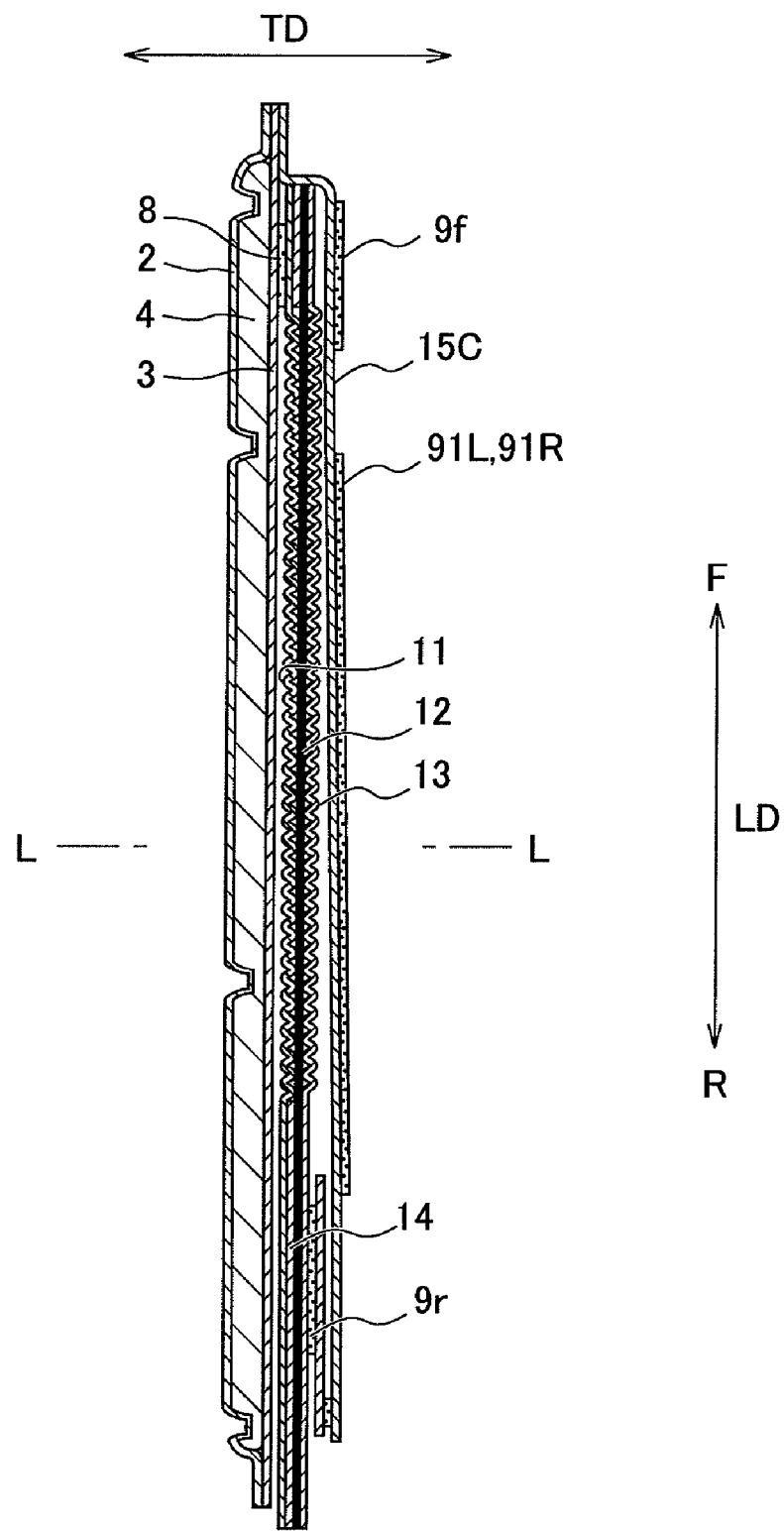
FIG. 16A is a sectional view taken along the line K-K of FIG. 15.
Figure 16B:
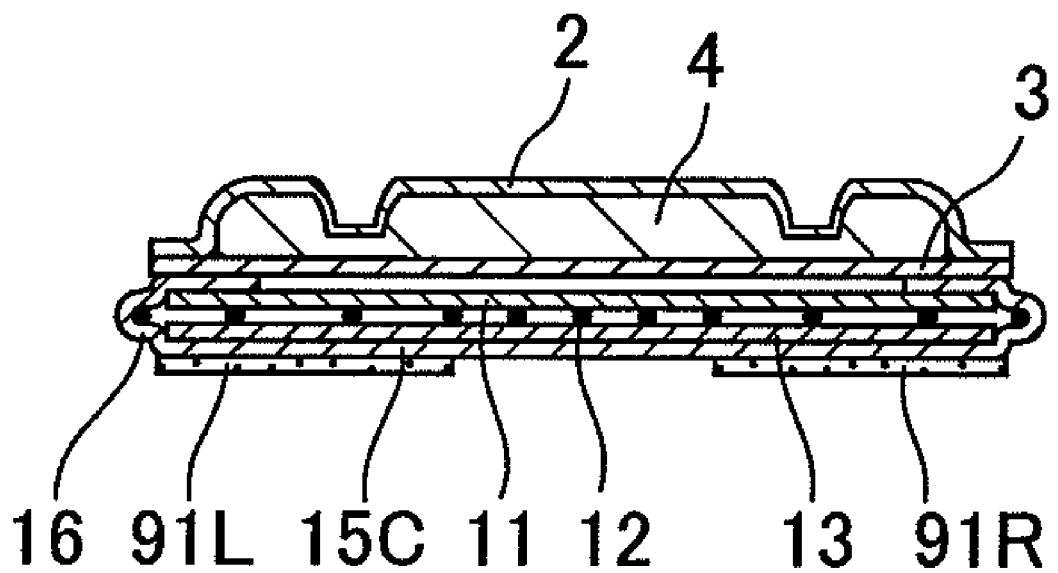
FIG. 16B is a sectional view taken along the line L-L of FIG. 15.
Figure 17:
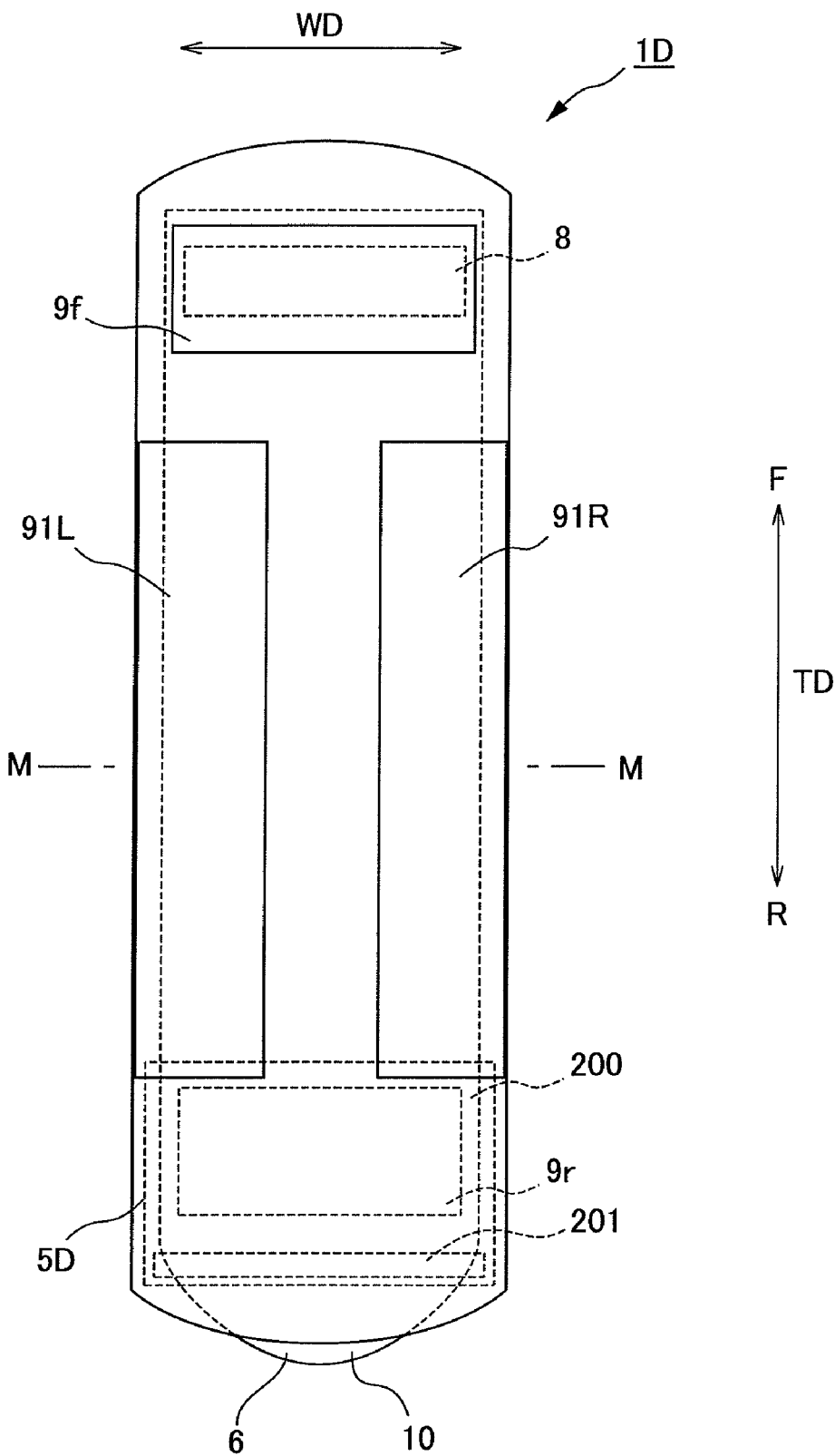
FIG. 17 is a back view of a sanitary napkin according to a fourth embodiment of the present invention.
Figure 18A:
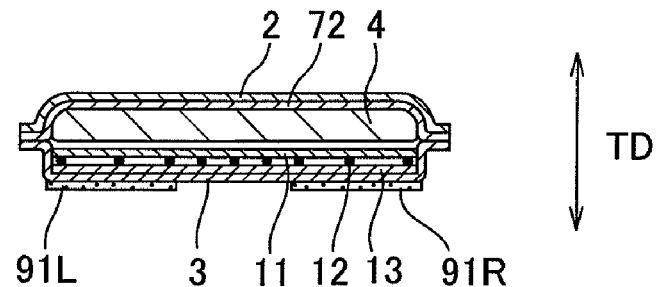
FIG. 18A is a sectional view taken along the line M-M of FIG. 17.
Figure 18B:
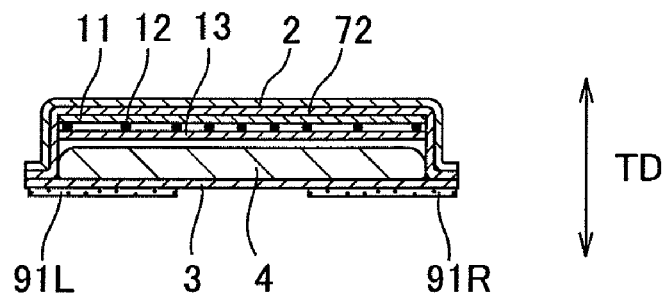
FIG. 18B is a sectional view illustrating another configuration of FIG. 18A.
Figure 19A:
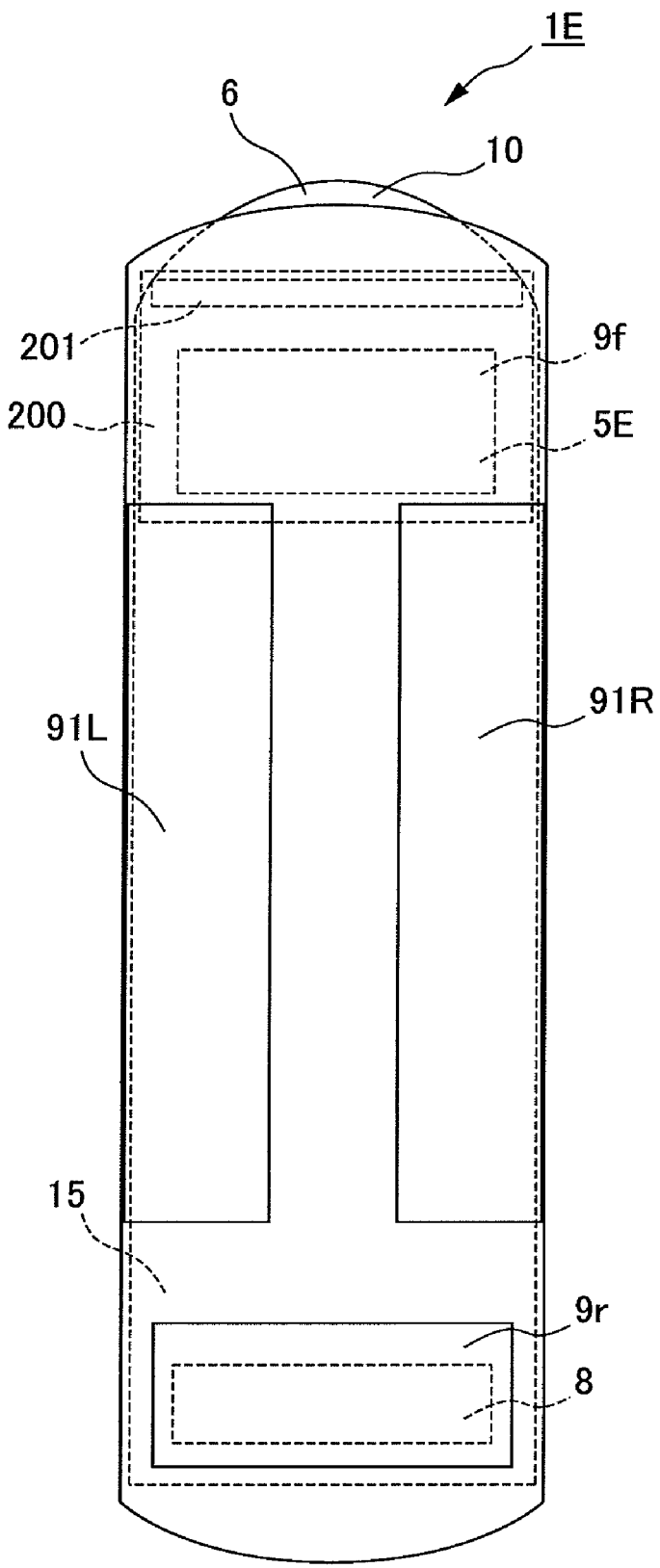
FIGS. 19A and 19B are back views of a sanitary napkin according to a fifth embodiment of the present invention.
Figure 19B:
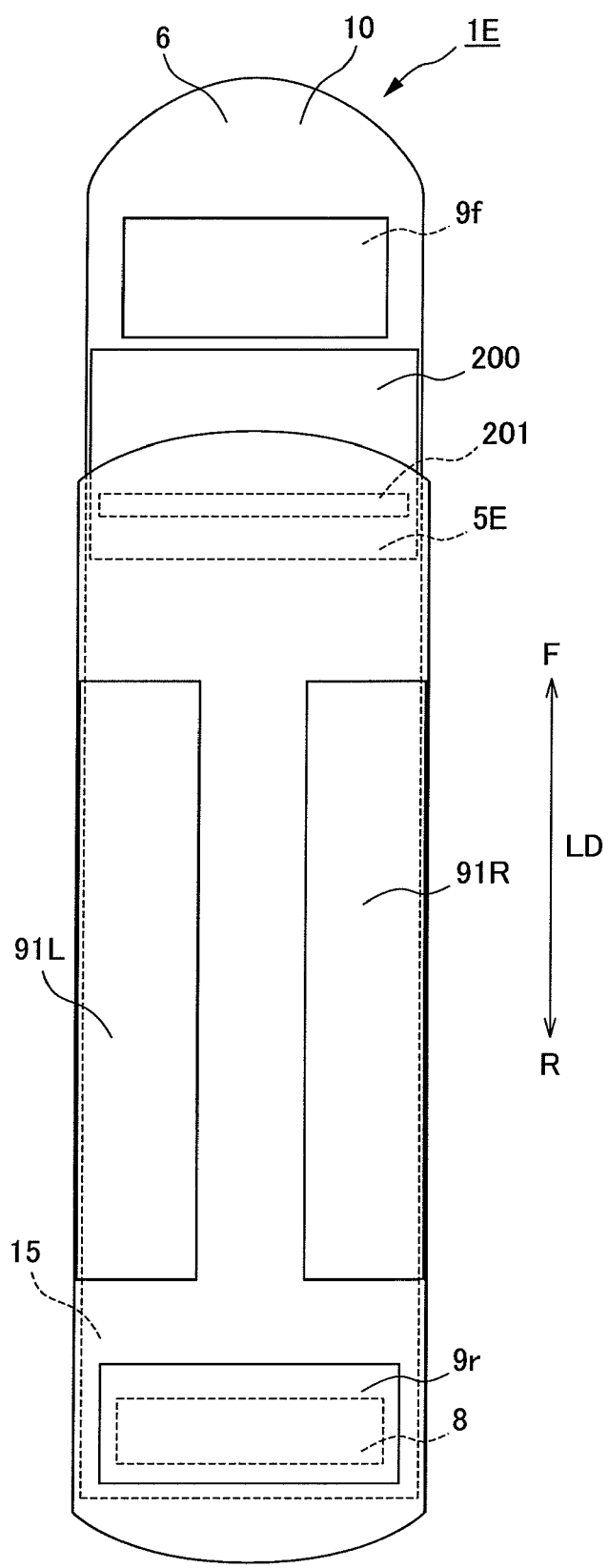

FIGS. 11A and 11B are partial sectional views illustrating the attached state of the sanitary napkin according to the first embodiment. FIG. 12A is a diagram illustrating a state where the sanitary napkin according to the first embodiment is attached; FIG. 12B is a sectional view taken along the line H-H of FIG. 12A; and FIG. 12C is a sectional view taken along the line I-I of FIG. 12A. FIG. 13 is a back view of a sanitary napkin according to a second embodiment of the present invention. FIG. 14A is a sectional view taken along the line J-J of FIG. 13; and FIG. 14B is a sectional view illustrating another configuration of FIG. 14A. FIG. 15 is a back view of a sanitary napkin according to a third embodiment of the present invention. FIG. 16A is a sectional view taken along the line K-K of FIG. 15; and FIG. 16B is a sectional view taken along the line L-L of FIG. 15. FIG. 17 is a back view of a sanitary napkin according to a fourth embodiment of the present invention. FIG. 18A is a sectional view taken along the line M-M of FIG. 17; and FIG. 18B is a sectional view illustrating another configuration of FIG. 18A. FIGS. 19A and 19B are back views of a sanitary napkin according to a fifth embodiment of the present invention.

Figure 20:
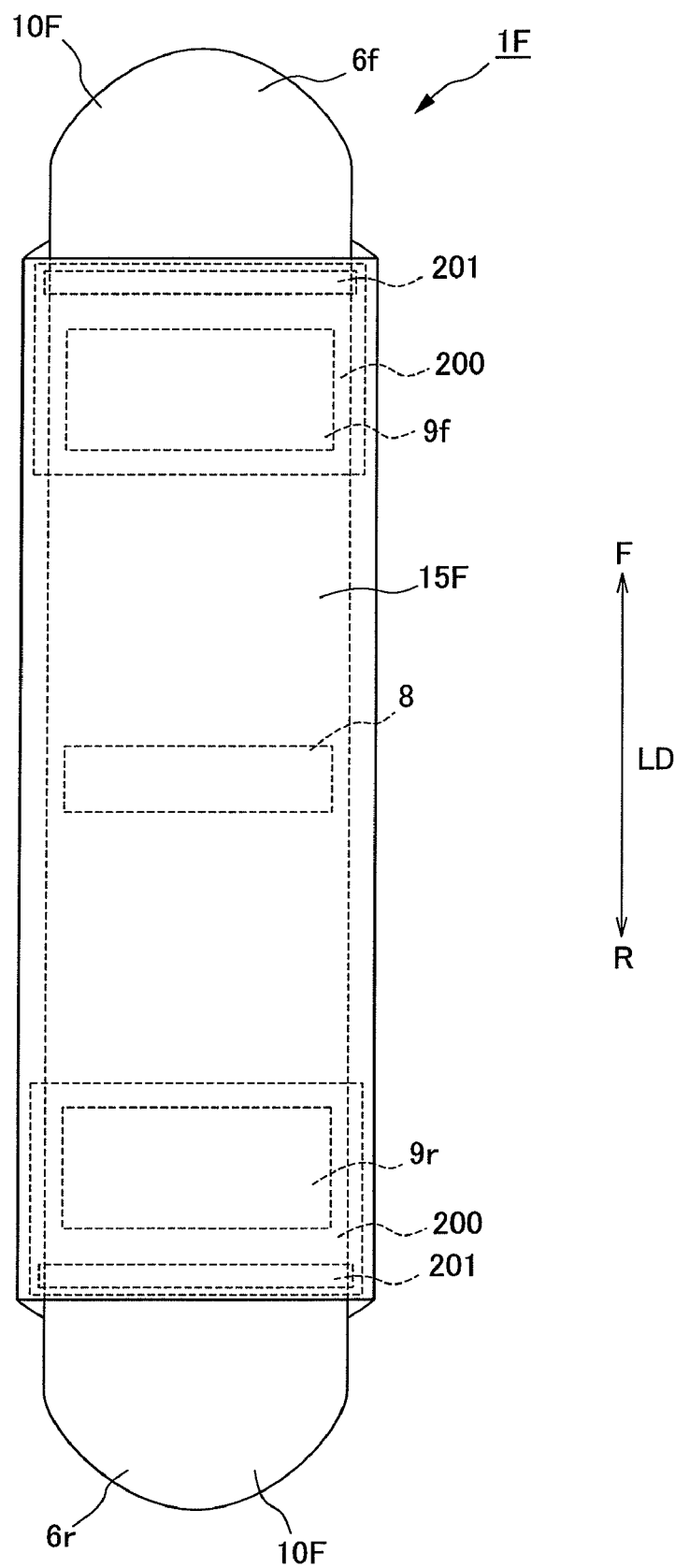
FIG. 20 is a back view of a sanitary napkin according to a sixth embodiment of the present invention.
Figure 21:
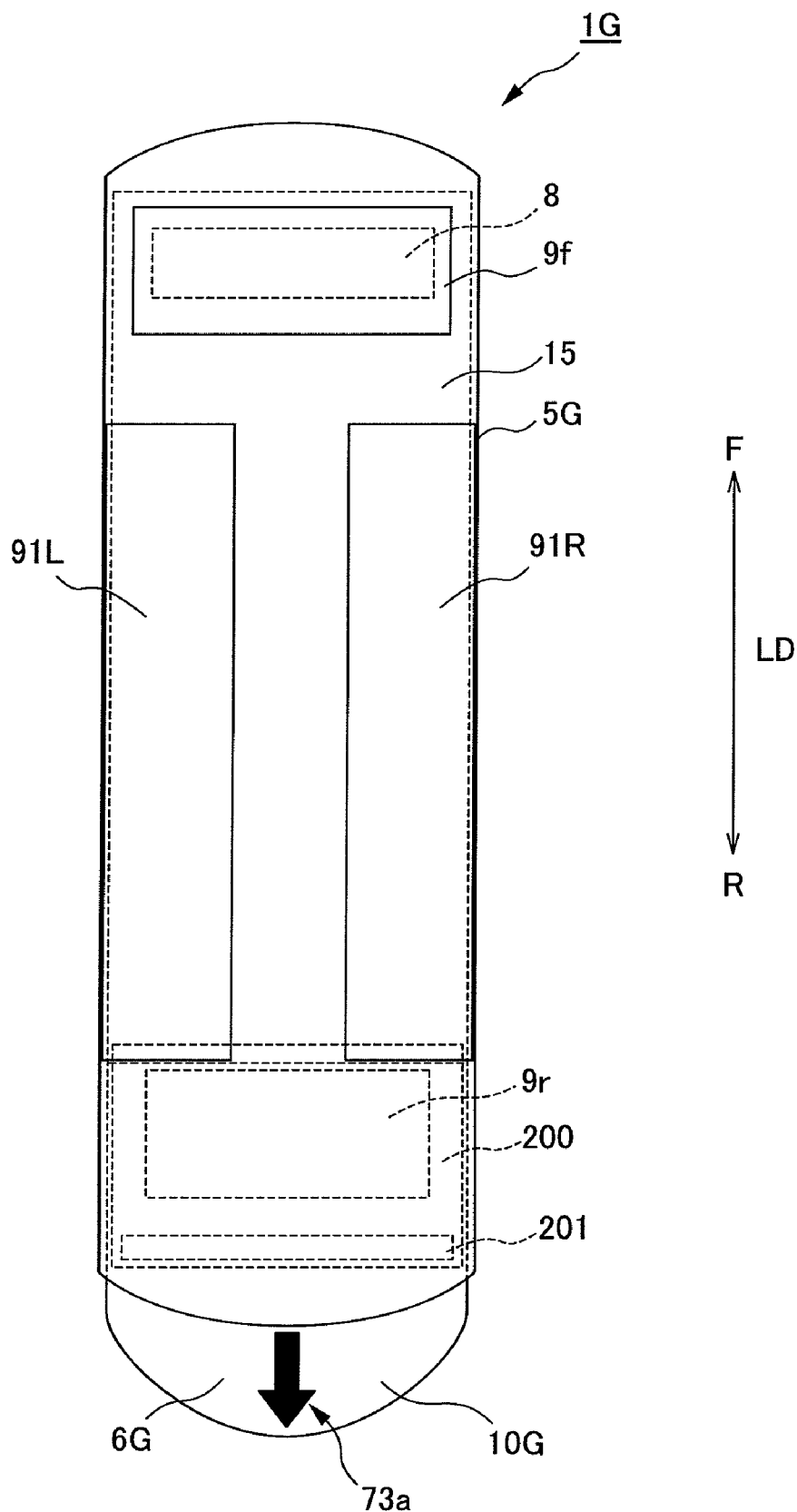
FIG. 21 is a back view of a sanitary napkin according to a seventh embodiment of the present invention.
Figure 22A:
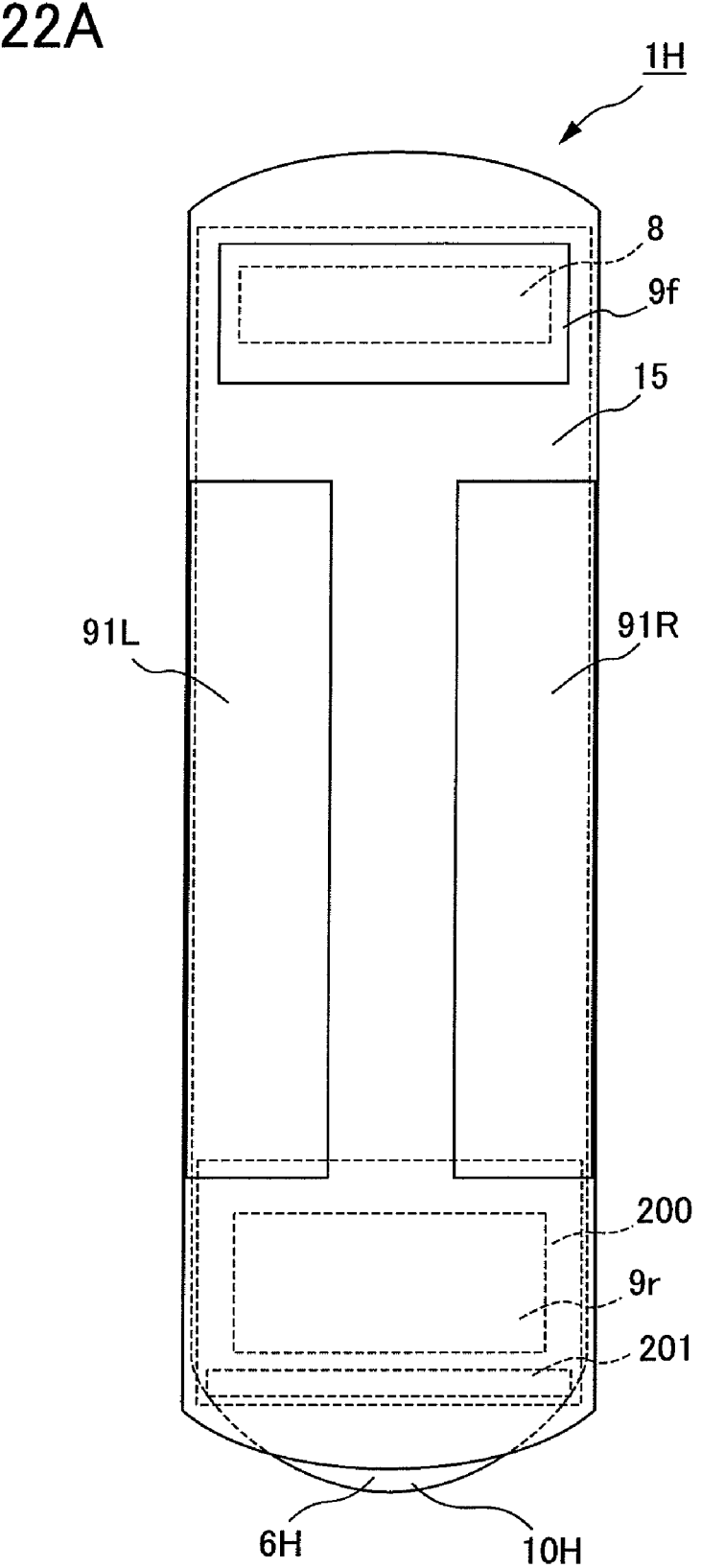
FIGS. 22A and 22B are back views of a sanitary napkin according to an eighth embodiment of the present invention.
Figure 22B:
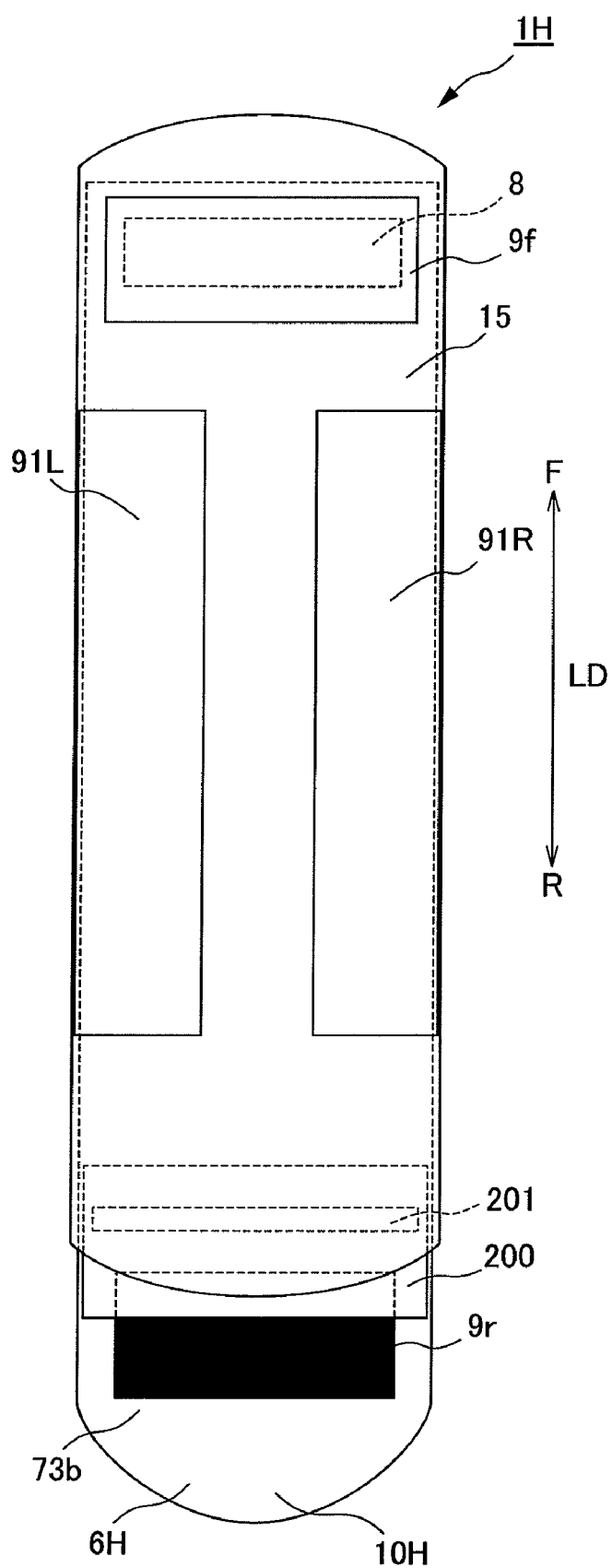
Figure 23B:
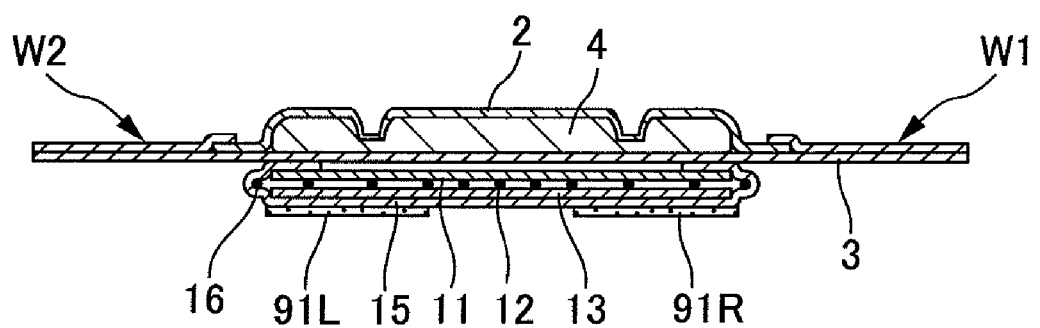
FIG. 23B is a sectional view taken along the line N-N of FIG. 23A.
Figure 24:
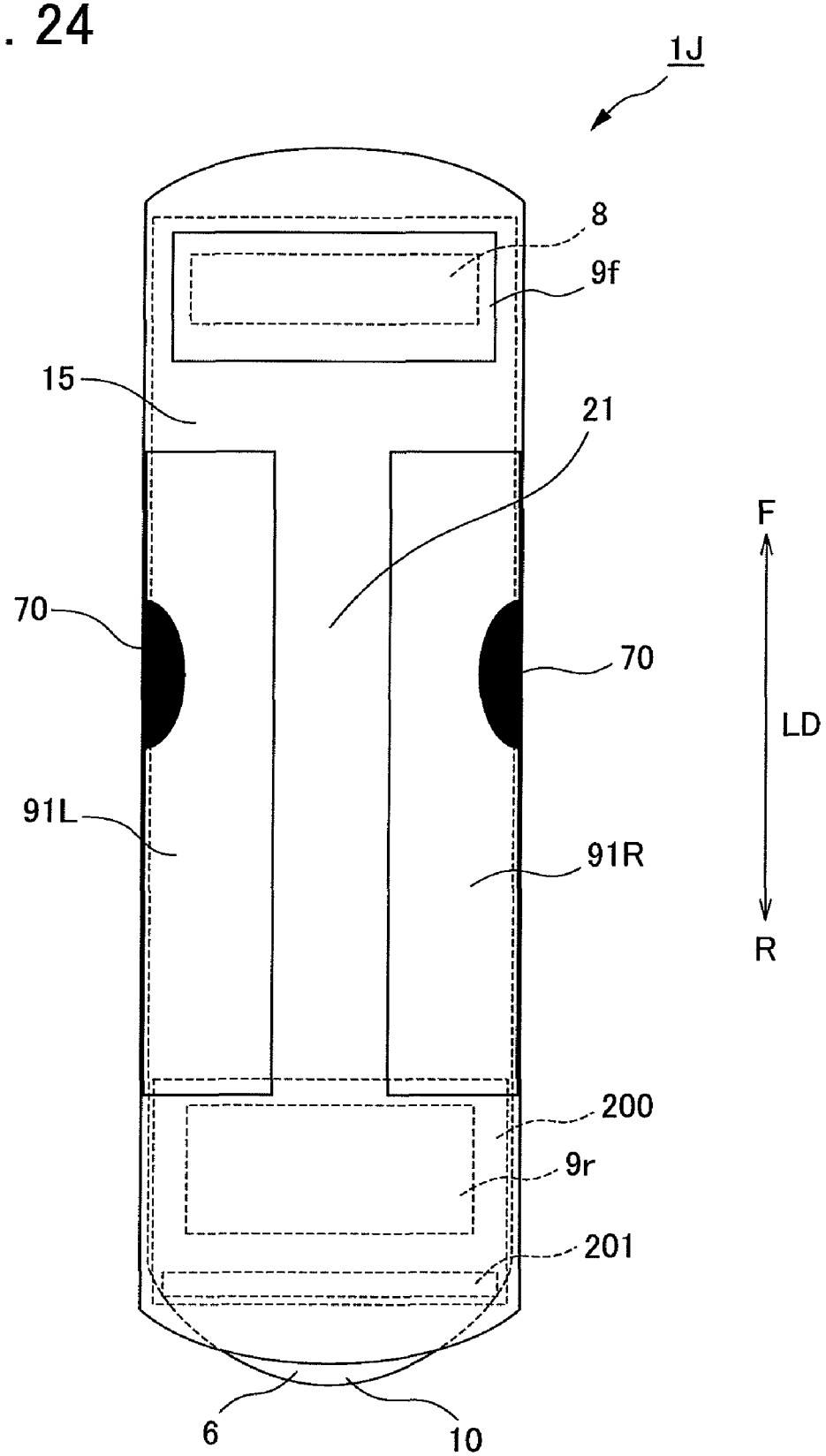
FIG. 24 is a back view of a sanitary napkin according to a tenth embodiment of the present invention.

FIG. 20 is a back view of a sanitary napkin according to a sixth embodiment of the present invention. FIG. 21 is a back view of a sanitary napkin according to a seventh embodiment of the present invention. FIGS. 22A and 22B are back views of a sanitary napkin according to an eighth embodiment of the present invention. FIG. 23A is a back view of a sanitary napkin according to a ninth embodiment of the present invention; and FIG. 23B is a sectional view taken along the line N-N of FIG. 23A. FIG. 24 is a back view of a sanitary napkin according to a tenth embodiment of the present invention. FIG. 25 is a back view of a sanitary napkin according to an eleventh embodiment of the present invention.

1. First Embodiment 1-1. Overall Configuration

The overall configuration of the absorbent article of the present invention will be described based on a sanitary napkin 1 according to a first embodiment of the present invention. In the first embodiment, the sanitary napkin 1 as the absorbent article has a sanitary napkin body 5 as an absorbent article body, a belt-shaped member 10, and a cover member 15 for covering the belt-shaped member 10. Specifically, as illustrated in FIGS. 1 to 4B, the sanitary napkin 1 has the sanitary napkin body 5, the belt-shaped member 10, and the cover member 15. The sanitary napkin body 5 has a liquid permeable top sheet part 2 which constitutes a surface layer and is disposed on the skin contact surface of a wearer, a liquid impermeable back sheet part 3 which constitutes a back layer and is disposed on the non-skin contact surface of the wearer, and a liquid retainable absorber part 4 which constitutes an absorption layer and is disposed between the top sheet part 2 and the back sheet part 3. The belt-shaped member 10 is disposed on the non-skin contact surface of the back sheet part 3, and is arranged along a longitudinal direction (LD) of the sanitary napkin body 5, on the non-skin contact surface (the other side) of the absorbent article body 5 in a thickness direction (TD). The cover member 15 covers at least a part of the belt-shaped member 10.

Specifically, the cover member 15 covers at least a part of the belt-shaped member 10 in the longitudinal direction (LD), and the entire of the belt-shaped member 10 in a width direction (WD). The belt-shaped member 10 is disposed slidably between the sanitary napkin body 5 and the cover member 15.

The sanitary napkin body 5 and the belt-shaped member 10 are connected to each other at a connecting part 8 provided on one end in the longitudinal direction (LD). Specifically, one end of the belt-shaped member 10 is connected to the back sheet part 3 at a predetermined position of a front region (F) of the sanitary napkin body 5, and the other end is provided with a free end 10r, which extends by using the connecting part 8 in a rear region (R) as the origin, along the longitudinal direction (LD) of the sanitary napkin body 5. As used here, the term "front region (f)" indicates the region extending from the vaginal opening to the abdominal part of the wearer when the sanitary napkin is worn. The term "rear region (R)" indicates the region extending from the vaginal opening to the buttocks of the wearer when the sanitary napkin is worn.

A free end 10r of the belt-shaped member 10 extends out of the outer edge portion of the sanitary napkin 5 in the longitudinal direction (LD). The portion so extended is provided with a grip part 6. An engaging part 9r to be engaged with the underwear 50 is disposed on the non-skin contact surface of the free end 10r of the belt-shaped member 10. The engaging part 9r is formed so that it can be covered with the cover member 15 when the belt-shaped member 10 is not stretched, and can be exposed when the belt-shaped member 10 is stretched. A peelable sheet 200, after being subject to mold releasing process, is connected onto a surface of the cover member 15 on which the belt-shaped member 10 is disposed. A peelable sheet 200 is arranged so as to cover the engaging part 9r of the belt-shaped member 10 when the belt-shaped member 10 is not stretched. The peelable sheet 200 is also connected to the cover member 15 in a fixing part 201 provided at an end portion of the cover member 15. Thus, the peelable sheet 200 can be separated from the engaging part 9r by stretching the belt-shaped member 10.

The sanitary napkin 1 of the present embodiment is further provided with a leakproof groove part 7 that can be formed by continuously compressing the top sheet part 2 and the absorber part 4.

1-2. Sanitary Napkin Body

The sanitary napkin body 5 is formed in a substantially elongated-shape. The sanitary napkin body 5 is, for example, a rectangle, an ellipse, and a guitar-shape, as well as a shape equipped with so-called wings W1 and W2 to be described later, which prevent dislocation from the underwear 50. The present invention may employ any shape suitable for the body of the wearer and the shape of the underwear 50. The length of the sanitary napkin body 5 in the longitudinal direction (LD) is, for example, from 100 to 500 mm, preferably from 150 to 350 mm. The length in the width direction (WD) is, for example, from 30 to 200 mm, preferably from 40 to 180 mm.

The sanitary napkin body 5 has a liquid permeable region 21 formed in a substantially elliptical shape at a substantially central part in the width section (WD) of the sanitary napkin body 5. The liquid permeable region 21 is surrounded by the leakproof groove part 7. The leakproof groove part 7 partitions the liquid permeable region 21. Excrement discharged from the excretory part, such as menstrual blood, passes through the top sheet part 2 in the liquid permeable region 21, and is then absorbed by the absorber part 4. Since the back sheet part 3 disposed on the non-skin contact surface is liquid impermeable, the excrement can be absorbed by the absorber part 4 and retained as is, without reaching the non-skin contact surface. A compressed part is formed in the leakproof groove part 7 by disposing areas of high compression and low compression continuously or at predetermined spaced intervals, so as to surround the liquid permeable region 21. The leakproof part 7 prevents mainly the leakage of excrement such as menstrual blood absorbed by the absorber part 4, and prevents the spread of excrement in the absorber part 4.

1-3. Belt-Shaped Member and Engaging Part

As shown in FIG. 5, the belt-shaped member 10 is formed in a substantially elongated-shape. The belt-shaped member 10 can be attained by sandwiching a plurality of thread-shaped elastic members 12 between a pair of belt-shaped base material sheets 11 and 13, and by bonding the base material sheets 11 and 13, respectively. Specifically, the belt-shaped member 10 can be formed by the following steps of: extending the elastic member 12 to a predetermined length by applying a predetermined tension in the longitudinal direction (LD) of the elastic member 12, and sandwiching the extended elastic member 12 between the base material sheets 11 and 13, followed by bonding.

The length of the belt-shaped member 10 in the width direction (WD) is preferably, for example, in the range of 30 to 150% of the length of the sanitary napkin body 5 in the width direction (WD), and more preferably in the range of 60 to 130%. This is because when it is below 30% of the length of the sanitary napkin body 5 in the width direction (WD), for example, the sanitary napkin body 5 cannot sufficiently contact the human body, even if the belt-shaped member 10 is stretched. This is also because when it is above 150%, the area to be contacted with the femoral region of the wearer is excessive, and skin irritation or the like might occur by frictional contact with the femoral region.

The length of the belt-shaped member 10 in the longitudinal direction (LD) is preferably, for example, in the range of 30 to 300% of the length of the sanitary napkin body 5 in the longitudinal direction (LD), and more preferably in the range of 70 to 150%. This is because when it is below 30% of the length of the sanitary napkin body 5 in the longitudinal direction (LD), the sanitary napkin body 5 cannot sufficiently contact the human body, even if the belt-shaped member 10 is stretched. This is also because when it is above 150%, the area to be contacted with the femoral region of the wearer is excessive, and skin irritation or the like might occur by frictional contact with the femoral region. Moreover, there is the likelihood that the belt-shaped member 10 in the extended state cannot be attached to the underwear 50, and cannot contact the excretory part.

The extensible range of the belt-shaped member 10 is preferably, for example, in the range of 105 to 300%, more preferably in the range of 110 to 180%, when the non-extended state of the elastic member 12 is 100%. This is because when the extended state is less than 105%, the force by which the sanitary napkin body 5 can be pressed to the human body is weak, and it is difficult to establish a structure for lifting the sanitary napkin body 5. This is also because when the extensible range is larger than 300%, an excessive push-up force to the human body than necessary is developed, and the wearer might feel discomfort. The stress of the elastic material 12 when the extended state is 105 to 300% in extension rate is preferably, for example, in the range of 5 to 500 cN/25 mm, and more preferably from 20 to 100 cN/25 mm.

The belt-shaped member 10 has the grip part 6 at the free end 10r, which is the end opposite the one end connected to the sanitary napkin body 5, in the longitudinal direction (LD) The grip part 6 is disposed so as to extend out of the outer edge portion of the sanitary napkin body 5. In order to facilitate the grip of the grip part 6 by the wearer, a sheet member 14 having a predetermined tensile strength may be interposed between the base material sheets 11 and 13, at a position corresponding to the grip part 6 of the belt-shaped member 10. The grip part 6 may be extended to a degree where the wearer can grip it by fingers. Preferably, the grip part 6 is disposed at an inextensible region.

Thus, the belt-shaped member 10 provided with the grip part 6 enables the wearer to easily recognize the belt-shaped member 10, enabling the prevention of mis-attachment at the time of the attachment.

The non-skin contact surface of the free end 10r in the belt-shaped member 10 is provided with the engaging part 9r. The engaging part 9r can be formed by coating with an engaging material having tackiness, as described later. Preferably, the engaging part 9r is arranged in the vicinity of the grip part 6 on the non-skin contact surface of the free end 10r of the belt-shaped member 10. For example, the length in the longitudinal length (LD) of the engaging part 9r on which the engaging material is coated is in the range of 5 to 50% of the longitudinal direction (LD) of the belt-shaped member 10. For example, the length in the width length (WD) of the engaging part 9r is in the range of 30 to 100% of the width direction (WD) of the belt-shaped member 10.

As shown in FIG. 6 and FIGS. 7A to 7C, in the belt-shaped member 10A, an absorbent member 100 may be disposed between the base material sheets 11 and 13, at the free end 10r including the grip part 6. Preferably, the absorbent member 100 is also arranged in a region to which the belt-shaped member 10A extends from the outer edge portion of the sanitary napkin body 5 when the belt-shaped member 10A is stretched. With this arrangement, even if excrement such as menstrual blood leaks from the sanitary napkin body 5 and effuses along the wearer's buttocks when attaching the sanitary napkin 1, it can be absorbed by the absorbent member 100 extending from the sanitary napkin body 5. Additionally, the absorbent member 100 so arranged enables the belt-shaped member 10A to also absorb the excrement that directly effuses along the wearer's buttocks.

In the region where the absorbent member 100 is arranged, it is preferable to provide a liquid impermeable sheet (not shown) on the non-skin contact surface of the belt-shaped member 10A, in the region corresponding to the absorbent member 100. This liquid impermeable sheet is preferably disposed so as to cover the outer edge portion on the free end 10r of the belt-shaped member 10A. Furthermore, the liquid impermeable sheet is arranged so as to cover at least a part on each of both sides of the belt-shaped member 10A. This enables soaking through of the excrement absorbed by the absorbent member 100 to the underwear 50 engaged to be prevented.

In cases where the extended elastic member 12 is included within the belt-shaped member 10, the extended elastic member 12 is bonded when sandwiched between the base material sheets 11 and 13, and then the extension of the elastic member 12 is released, an extension allowance can be formed in the base material sheets 11 and 13. The extension allowance enables the belt-shaped member 10 to be extended. The term "extension allowance" includes sag and looseness developed in the base material sheets 11 and 13 when these are shrunk by releasing the extension of the elastic member 12 connected to the base material sheets 11 and 13. The belt-shaped member 10 can be extended by the amount of sag or the like. In addition, the belt-shaped member 10, in which the elastic member 12 is sandwiched between the inflexible base material sheets 11 and 13, is able to prevent so-called neck in, namely the phenomenon that, for example, when a belt-shaped elastic member is stretched, the substantially central part thereof becomes narrow.

As another extension process of the belt-shaped member 10, it may be made extensible by performing a partial slitting process or embossing finish.

FIGS. 8 and 9A show a belt-shaped member 10A-1 subjected to a corrugated embossing finish. As shown in FIGS. 8 and 9A, the corrugated embossing finish produces a corrugated pattern where irregularities are continuously formed in the longitudinal direction (LD). The pitch between the convex portions is, for example, from 0.5 to 5.0 mm. The height of the convex portions is, for example, from 0.5 to 5.0 mm. The clearance between the convex side surfaces in meshing engagement is, for example, from 0 to 3.0 mm.

The corrugated embossing can be formed with the base material sheets 11 and 13 sandwiched between a pair of embossing rolls provided with a lower roll part having a continuous concave part on a surface thereof, and an upper roll part having a continuous convex on the surface thereof, and allowing the concave part and the convex part to mesh with the base material sheets 11 and 13. This enables extensibility to be imparted. When employing the corrugated embossing finish, the belt-shaped member 10A-1 may be formed with the elastic member 12 sandwiched between the base material sheets 11 and 13, in a state where the elastic member 12 is stretched or not extended.

The belt-shaped member 10 thus formed can facilitate the setting of the extension range thereof. For example, when the extension range is set to 130% of the non-extended state, a base material sheet may be used which has a length of 130% when it is stretched, and the concave and convex shapes of corrugated embossing may be formed in this base material sheet. Alternatively, the elastic material 12 having a maximum extension of 130% may be sandwiched in its extended state between the base material sheets 11 and 13. For example, when the extension range is 130% of the non-extended state, the wearer can easily pull the belt-shaped member 10 up to 130% elongation, with pulling more than that requiring excess power. Thus, the belt-shaped member 10 enables the wearer to recognize the extension range by letting the wearer find a difficult-to-pull point in the extension range. By setting the extension range of the belt-shaped member 10, the sanitary napkin 1 can be put on properly by the user.

In order to impart regularity to the extension allowance, as illustrated in FIG. 9B, blanks 30 (areas having neither a concavity nor a convexity) may be provided partially in the width direction (WD), to the corrugated embossing pattern of the base material sheets 11 and 13 in a belt-shaped member 10A-1. Specifically, in addition to the embossing pattern shown in FIG. 5, blanks 30 having a width of 0.5 to 3.0 mm may be formed at pitches of 5 to 40 mm in the width direction (WD). Alternatively, the blanks 30 may be formed by coating a base material with a hot melt in the coating pattern that coating is carried out continuously in the width direction (WD), and repeatedly coating and not coating in the longitudinal direction (LD).

Although the present embodiment employs the inextensible material as the base material sheets 11 and 13, without limiting to this, the present invention may employ, for example, an extensible material or a flexible material. Although in the present embodiment, the belt-shaped member 10 is made up of the base material sheets 11 and 13, and the elastic material 12, without limiting to this, the present invention may employ only a flexible base material sheet. For example, it is possible to employ a fibrous sheet using thermoplastic elastomer resin, a non-woven fabric obtained by mixing urethane fiber and a synthetic fiber, a non-woven fabric including a layer obtained by forming elastomer resin by melt blowing, a film sheet, or the like.

There is no need to provide the elastic material 12 in the entire region of the base material sheets 11 and 13, and it may be provided in at least a part of the region. For example, the region of the engaging material as the engaging part with the underwear 50 may be constituted of the base material sheets 11 and 13, and the rest may be configured so that the elastic member 12 is sandwiched between the sheets 11 and 13. In addition, the region constituting the grip part 6, as described later, may be constituted of the base material sheets 11 and 13, without sandwiching the elastic material 12 in between.

The belt-shaped member 10 is also required to have a flexible region in at least a portion of the longitudinal direction (LD). Preferably, the belt-shaped member 10 is flexible at a position where the sanitary napkin body 5 contacts the excretory part. More preferably, the belt-shaped member 10 is flexible at a position where the sanitary napkin body 5 is adhered to the vaginal opening. More specifically, at the time of the attachment, the belt-shaped member 10 may include an inflexible region in a portion of the longitudinal direction (LD). For example, the region where the back sheet part 3 and the belt-shaped member 10 are connected to each other, and the region where the sanitary napkin body 5 or the belt-shaped member 10 is engaged with the underwear 50, may be inflexible, and the rest may be flexible. In the absence of any flexibility in the connecting part 8 and the engaging parts 9f and 9r, the connecting material for connecting the back sheet part 3 and the belt-shaped member 10, and the engaging material for engaging the belt-shaped member 10 and the underwear 50, are difficult to separate.

The inflexible region may be formed, for example, by connecting the elastic material 12 in the non-extended state, with the base material sheets 11 and 13. The elastic material 12 in the extended state may be cut to eliminate elastic force. Alternatively, extensible regions generated by the corrugated embossing finish may be connected together to form the inflexible region. The base material sheets 11 and 13 may be inflexible without applying a process for forming a flexible region, such as the corrugated embossing finish of the base material sheets 11 and 13.

The belt-shaped member 10 may be formed of a non-stretchable sheet. In this case, as shown in FIG. 10, a sanitary napkin 1A may use a belt-shaped member 10A-2 formed of a non-stretchable sheet provided with a predetermined folding part 17. Examples of the non-stretchable sheet are a non-woven fabric and a film sheet. The belt-shaped member 10A-2 is required to be tensile strength enough to withstand the stress exerted when lifting the belt-shaped member 10A-2. Although the non-stretchable sheet may be in the shape of a belt-shape or a string-shape, the belt-shape is preferred.

Therefore, the belt-shaped member 10A-2 may be configured to be stretchable by providing the folding part 17 for folding by a predetermined amount. Arranging the belt-shaped member 10A-2 in the folded state enables the belt-shaped member 10A-2 to have a predetermined length, and to be accommodated in a compact form.

For example, the predetermined length is preferably in the range of 30 to 300% of the length in the longitudinal direction of the sanitary napkin body, and more preferably in the range of 70 to 150%. The predetermined amount in the folding part 17 includes the length that permits folding back for maintaining the predetermined length of the belt-shaped member 10A-2.

1-4. Cover Member

A cover member 15 is connected to the sanitary napkin body 5 at both side portions and an outer edge portion within the front region (F) in the sanitary napkin body 5. More specifically, the cover member 15 has a configuration in which the end portion in the rear region (R) is opened.

Alternatively, the cover member 15 may be connected to the sanitary napkin body 5 at both side portions of the sanitary napkin 1 and the outer edge portion within the front region (F), in a state where the cover member 15 extends from both side portions and the outer edge portion within the front region (F) in the sanitary napkin body 5, respectively.

The length of the cover member 15 in the longitudinal direction (LD) is preferably, for example, in the range of 10 to 100% of the length of the sanitary napkin body 5C in the longitudinal direction (LD), and more preferably in the range of 50 to 90%. This is because when it is below 10%, the degree of freedom between the sanitary napkin body 5C and the belt-shaped member 10 is too large, and slippage might occur in use. This is also because when it is above 100%, the cover member 15 might be an obstacle in the operation of extending and engaging the belt-shaped member 10 with the underwear 50.

The length of the cover member 15 in the width direction (WD) is preferably, for example, in the range of 30 to 150% of the length of the sanitary napkin body 5 in the width direction (WD), and more preferably in the range of 50 to 110%. This is because when it is below 30%, the sanitary napkin body 5 cannot sufficiently contact the human body. This is also because when it is above 150%, the area to be contacted with the femoral region is excessive, and therefore skin irritation due to frictional contact or the like might occur.

The length of the cover member 15 in the width direction (WD) is preferably, for example, in the range of 100 to 200% of the length of the belt-shaped member 10 in the width direction (WD), and more preferably in the range of 105 to 150%. This is because when it is below 100%, the belt-shaped member 10 cannot be extended smoothly. This is also because when it is above 200%, the degree of freedom of the belt-shaped member 10 in the width direction (WD) is too large, and therefore misalignment between the central axis of the sanitary napkin body 5 and the central axis of the belt-shaped member 10 might occur.

The cover member 15 may be formed of a different material from the construction materials of the sanitary napkin body 5. Alternatively, any one of these construction materials may also be used for forming the cover member 15. In this case, a common construction material may be elongated so as to continuously form the cover member 15. For example, the top sheet part 2 or the back sheet 3 may be used successively. In this case, the respective sheets disposed continuously may be overlapped and connected to each other on the non-skin contact surface. For example, at least 50% of the length of the sanitary napkin body 5 in the width-direction (WD) may be extended, and the respective extended sheets may be folded back to connect them in a stacked state, at the substantially central part in the width direction (WD) on the non-skin contact surface of the sanitary napkin body 5.

In the case when both side portions of the cover member 15 are folded back to connect to the sanitary napkin body 5, elastic members stretchable in the longitudinal direction (LD) may be arranged at fold-back portions on both side portions.

In this case, even if a force to twist the fold-back portions is exerted in the width direction (WD) of the sanitary napkin body 5 or the cover member 15, the restoring force of the elastic members enables the suppression of the abovementioned force.

Alternatively, the cover member 15 may be made flexible in the width direction (WD) of the sanitary napkin 1. This is because the belt-shaped member 10 can be held within the cover member 15. This is also because, when the belt-shaped member 10 is stretched, it is stretchable so as to be easily pulled. Additionally, even if a relative slippage between, for example, the underwear and the human body occurs due to loosening of the underwear or deformation by way of human body movement, the cover member 15 will follow for the slippage, and extend or retract, and therefore it is able to retain a closely contacted state between the human body and the sanitary napkin body 5. As an alternative, the entire or a part of the cover member 15 may be made flexible. For example, the vicinity of the open portion of the cover member 15 in the rear region (R) may be made flexible.

1-5. Peelable Sheet and Fixing Part

A peelable sheet 200 is connected to the cover member 15. Specifically, the peelable sheet 200 is arranged so as to cover the entire engaging part 9r and connect to the cover member 15, in a fixing part 201 disposed in the rear region (R) of the cover member 15. The peelable sheet 200 may be connected to the cover member 15 by using hot melt adhesive, or by way of an embossing finish or sonic process. Thus, by covering the engaging part 9r with the peelable sheet 200, the engaging part 9r can be encased by the cover member 15. When the engaging part 9r is coated with adhesive, for example, sticking the engaging part 9r to any unintended location is avoidable. Furthermore, by using the fixing part 201 to connect the peelable sheet 200 and the cover member 15, the peelable sheet 200 can be separated from the engaging part 9r with the stretch of the belt-shaped member 10, thus facilitating the engagement of the engaging part 9r to the underwear 50.

The length of the peelable sheet 200 in the longitudinal direction (LD) is preferably, for example, in the range of 100 to 300% of the length of the engaging part 9r in the longitudinal direction (LD), and more preferably in the range of 10 to 200%. The length of the peelable sheet 200 in the width direction (WD) is preferably, for example, in the range of 100 to 300% of the length of the engaging part 9r in the width direction (WD), and more preferably in the range of 100 to 200%.

The length of the fixing part 201 in the longitudinal direction (LD) is preferably, for example, in the range of 1 to 50% of the length of peelable sheet 200 in the longitudinal direction (LD), and more preferably in the range of 2 to 10%. The length of the fixing part 201 in the width direction (WD) is preferably, for example, in the range of 30 to 100% of the length of the peelable sheet 200 in the width direction (WD), and more preferably in the range of 50 to 100%.

1-6. Positional Relationship between Fixing Part and Engaging Part

Referring to FIGS. 11A and 11B, the position to provide the fixing part 201 is preferably between an end portion 210 in the rear region (R) of the cover member 15 and an end portion 211 in the rear region (R) of the engaging part 9r of the belt-shaped member 10. In other words, as illustrated in FIG. 11B, the fixing part 201 is arranged at a position further adjacent to the rear region (R) of the cover member 15 than the end portion 211 in the rear region (R) of the engaging part 9r of the belt-shaped member 10. Specifically, an end portion 212 in the rear region (R) of the fixing part 201 is arranged at a position corresponding to the end portion 211 in the rear region (R) of the engaging part 9r, or a position to the rear of end portion 211 by at least 1 mm, preferably by 1 to 50 mm, and more preferably by 5 to 20 mm. Thus, with the abovementioned positional relationship between the fixing part 201 and the end portion 211 of the engaging part 9r in the belt-shaped member 10, there are the following advantages, for example. That is, as illustrated in FIG. 11A, when the belt-shaped member 10 is extended, the peelable sheet 200 can be separated from the engaging part 9r by using the fixing part 201 as the starting point. As a result, the engaging part 9r can be exposed, and it is, therefore, easy to adhere the belt-shaped member 10 to the underwear 50.

1-7. Position to Connect Sanitary Napkin Body and Belt-Shaped Member

The sanitary napkin body 5 and the belt-shaped member 10 are connected at the connecting part 8. The position to connect the belt-shaped member 10 and the sanitary napkin body 5 is preferably in the front region (F) away from the wearer's vaginal opening when the sanitary napkin 1 is put on. For example, the position to connect is preferably located at a swelling part present in the vicinity of the wearer's excretory part. Specifically, the position to connect is preferably the position corresponding to the pubis present in the vicinity of the excretory part. Since the position corresponding to the pubis is harder than the surroundings and slightly swelled, the pressure from the underwear 50 can be increased thereby to suppress slippage of the sanitary napkin body 5 from the human body. Thus, even if the belt-shaped member 10 is pulled and extended at the time of the attachment, the sanitary napkin body 5 cannot be bent due to the stress induced at that time. As a result, it is difficult for the sanitary napkin body 5 to slip at the time of attachment, and when the sanitary napkin 1 is put on.

In the connecting part 8, the sheet member 14 having a predetermined tensile strength may be sandwiched between the base material sheets 11 and 13. This can impart a predetermined strength to the connecting part 8, enabling the connection of the belt-shaped member 10 to be stabilized.

1-8. Position to Engage Belt-Shaped Member and Underwear

The belt-shaped member 10 has the engaging parts 9f and 9r to be engaged with the underwear 50 at both ends in the longitudinal direction (LD), respectively. The engaging part 9f is engaged with the underwear 50 or the like in the front region (F), and the engaging part 9r is engaged with the underwear 50 in the rear region (R). Preferably, the engaging part 9f is provided at a position opposing the connecting part 8, where the sanitary napkin body 5 and the belt-shaped member 10 are connected to each other. This is because the connecting part 8 for connecting the sanitary napkin body 5 and the belt-shaped member 10 is the origin of the belt-shaped member 10 to the free end 10r, and also the point where the tension of the belt-shaped member 10 to the sanitary napkin body 5 is maximized. At this point, it is difficult for the sanitary napkin body 5 to slip from the underwear 50.

Preferably, the engaging part 9r is located slightly ahead of the rearmost end in the rear end part of the belt-shaped member 10. The reasons for this are as follows. Since the human body is often greatly curved from the vaginal opening to the rear, the belt-shaped member 10 lying at the rear side allows for the expansion of the flexible range of the belt-shaped member 10. The extension of the belt-shaped member 10 along the curvature of the human body facilitates the transmission of the stress on the belt-shaped member 10 to the sanitary napkin body 5 located in the vicinity of the excretory part. In addition, by disposing the engaging part 9r slightly ahead of the rearmost end in the rear end part of the belt-shaped member 10, it is also possible to prevent the engaging material from being adhered to the finger or the like when the wearer grips the grip part 6.

Examples of the engaging material used for the engaging parts 9f and 9r are a hot melt adhesive, hook material, and binder. The engaging material used for the engaging part 9r disposed in the rear region (R) may be the engaging material to be engaged with the underwear 50 or the wearer's body. That is, the engaging part may be engaged with the underwear 50 or the like, or alternatively engaged with the wearer's body.

In order to avoid the belt-shaped member 10 slipping from the underwear or the like when the sanitary napkin 1 is worn, when the belt-shaped member 10 has flexibility, the engaging force of the engaging material is required to be larger than the contractive force of the belt-shaped member 10. Accordingly, the shear stress that is the engaging force is preferably set to be larger than the contractive force in the range of 5 to 500 cN/25 mm.

1-9. Manner of Use

Manners of use of the sanitary napkin 1 in the first embodiment of the present invention are described with reference to FIGS. 12A to 12C. Specifically, there are first and second manners of use of the sanitary napkin 1.

In the first manner of use, the sanitary napkin 1 is first arranged at a predetermined position of the underwear 50, and the engaging part 9f in the front region (F) on the non-skin contact surface of the sanitary napkin 1 is engaged to the underwear 50. The term "predetermined position of the underwear 50" includes, for example, an expected position where the liquid permeable region 21 in the sanitary napkin 1 can be brought into contact with the wearer's excretory part.

Subsequently, the grip part 6 disposed on the free end 10r of the belt-shaped member 10 is pulled to the rear region (R) in the longitudinal direction (LD), while pressing against the underwear 50 and the sanitary napkin 1, which are located at the engaging part 9f in the front region (F) of the sanitary napkin 1. As a result, the belt-shaped member 10 can be stretched, and the engaging part 9r arranged on the non-skin contact surface of the belt-shaped member 10 can be exposed. Here, since the peelable sheet 200 covering the engaging part 9f is connected to the cover member 15, the peelable sheet 200 can be separated from the engaging part 9r with the fixing part 201 as the starting point, by pulling the belt-shaped member 10 so as to shift the engaging part 9r. The engaging part 9r thus exposed is then stuck to a predetermined position of the underwear 50 so that the extended portion of the belt-shaped member 10 corresponds to the wearer's excretory part. At this time, the engaging part 9r is preferably stuck to the underwear 50 with the belt-shaped member 10 stretched as much as possible.

In the state of completion of the attachment of the sanitary napkin 1, the underwear 50 is put on, so that the belt-shaped member 10 and the sanitary napkin 5 can be deformed in a gentle curve, and stress can be transmitted from the belt-shaped member 10 to the sanitary napkin body 5 in the direction of the wearer's body. At this time, the belt-shaped member 10 pushes the sanitary napkin body 5 up so as to lift it to the human body. This enables the adhesion of the wearer's excretory part and the groove in the vicinity of the excretory part to the sanitary napkin 1 (refer to FIGS. 12A to 12C).

In the second manner of use, the sanitary napkin 1 is arranged at the same position as in the first manner of use, and fixed to the underwear 50. Specifically, the sanitary napkin 1 is arranged at a predetermined position of the underwear 50, and an engaging material disposed at the engaging part 9f in the front region (F) on the non-skin contact surface of the sanitary napkin 1 is engaged to the underwear 50. In this state, the wearer puts on the underwear 50. Subsequently, the wearer grips the grip part 6 of the belt-shaped member 10 extending to the rear region (R) on the internal surface of the underwear 50, and engages the engaging part 9r to a predetermined position of the underwear 50 by pulling the grip part 6 in the longitudinal direction, along the curvature of the human body.

At this time, the underwear 50 is in the state of being lifted to the human body together with the sanitary napkin 1. Therefore, the free end 10r of the belt-shaped member 10 is pulled to engage the sanitary napkin 1 with the underwear 50, and the position can be adjusted so that the belt-shaped member 10 contacts the groove in the vicinity of the wearer's excretory part (refer to FIGS. 12A to 12C).

Therefore, since the underwear 50 and the belt-shaped member 10 are fixed to each other by gripping the grip part 6 and pulling the belt-shaped member 10 to the rear region (R), tension can be exerted on the belt-shaped member 10 in the longitudinal direction (LD). When the belt-shaped member 10 is brought near the human body, the belt-shaped member 10 and the sanitary napkin 5 can be deformed in a gentle curve, and pressure can be transmitted from the belt-shaped member 10 to the sanitary napkin body 5 in the direction of the wearer's body. At this time, the belt-shaped member 10 pushes up the sanitary napkin body 5 so as to lift it to the human body. As a result, the wearer's excretory part and the groove in the vicinity of the excretory part can contact the sanitary napkin 1.

The flexibility of the belt-shaped member also provides the following advantage. That is, even if a relative slippage between underwear and the human body occurs due to loosening of the underwear or deformation along with body movement, the cover member 15 will follow for the slippage, and extend or retract, and it is, therefore, able to retain a state of close contact between the human body and the absorber body. This improves the contact between the wearer's excretory part, etc. and the absorbent article, thereby preventing leakage of excrement such as menstrual blood.

2. Other Embodiments

The second to eleventh embodiments of the present invention are described with reference to FIGS. 13 to 25. The second embodiment shows another embodiment relating to the location of the cover member 15. The third embodiment shows another embodiment where the cover member 15 is provided with an engaging part. The fourth embodiment shows another embodiment relating to the location of the belt-shaped member 10. The fifth embodiment shows another embodiment relating to the direction of stretch of the belt-shaped member 10. The sixth embodiment shows a still another embodiment relating to the direction of stretch of the belt-shaped member 10. The seventh and eighth embodiments show other embodiments relating to the guide element of the belt-shaped member 10. The ninth and tenth embodiments show other embodiments for implying the liquid permeable region 21 of the sanitary napkin body 5. The eleventh embodiment shows another embodiment relating to the arrangement of the belt-shaped member 10.

In the following description, the same reference numerals have been retained for similar parts that are identical to that described in the first embodiment, with the description thereof omitted.

2-1. Second Embodiment

A sanitary napkin 1B in the second embodiment of the present invention is described with reference to FIGS. 13 and 14. As illustrated in FIGS. 13 and 14, a sanitary napkin 1B is different from the first embodiment in that a cover member 15B is partly arranged in a sanitary napkin body 5B. Specifically, in the sanitary napkin 1B, the cover member 15B is provided in the rear region (R). By providing the cover member 15B only in the rear region (R) of the sanitary napkin body 5B, the resistance induced by sliding the belt-shaped member 10 can be reduced. This facilitates, for example, extension and retraction of the belt-shaped member 10.

In the second embodiment, the cover member 15B is provided so as to cover the engaging part 9r of the belt-shaped member 10. In this case, when the belt-shaped member 10 is in an inflexible state, the grip part 6 of the belt-shaped member 10 extends from the outer edge portion in the rear region (R) in the longitudinal direction (LD) of the sanitary napkin body 5B, and the engaging part 9r is covered with the cover member 15B. This prevents, for example, the engaging part 9r from sticking to any unintentional location before the belt-shaped member 10 is stretched. Additionally, the extension of the grip part 6 enables, for example, the wearer to easily pinch the grip part 6, thereby increasing ease of operability. The cover member 15B is also provided with the peelable sheet 200 arranged so as to cover the engaging part 9r. The peelable sheet 200 is connected to the end portion in the direction of elongation of the belt-shaped member 10 in the cover member 15B. With this arrangement, the peelable sheet 200 can easily be separated from the engaging part 9r by stretching the belt-shaped member 10.

A plurality of the cover members 15B may be provided. Alternatively, the cover member 15B may be arranged so as to cover a part of the sanitary napkin body 5B. The cover member 15B is required to cover at least the engaging part 9r provided in the belt-shaped member 10. Preferably, the cover member 15B is arranged in the vicinity of the rear region (R) of the sanitary napkin body 5B. This is because it is possible to prevent slippage of the belt-shaped member 10 from the sanitary napkin body 5B during use of the sanitary napkin 1B.

Referring to FIG. 14B, the cover member 15 may be folded back at both side portions in the width direction (WD) of the sanitary napkin body 5B, and elastic members 16 may be arranged at the fold-back portions, respectively. In this case, even if the sanitary napkin body 5B or the belt-shaped member 10 has a tendency to twist, the elasticity of the elastic members 16 produces a force to restore the belt-shaped member 10 from the twist, thereby preventing the twist of the sanitary napkin body 5B or the belt-shaped member 10.

2-2. Third Embodiment

A sanitary napkin 1C in the third embodiment of the present invention is described with reference to FIGS. 15 and 16. As illustrated in FIGS. 15 and 16, the sanitary napkin 1C is different from the first embodiment in that the engaging parts 91R and 91L to be engaged to the underwear 50 are provided at both side portions in the width direction (WD) of a cover member 15C, respectively.

Therefore, with the engaging parts 91R and 91L arranged at both side portions of the cover member 15C, the underwear 50 can also be lifted to the human body by the tension of the belt-shaped member 10. This prevents, for example, dislocation between the sanitary napkin 1C and the underwear 50.

A plurality of (e.g., two in number) the engaging parts 91R and 91L may be arranged on each of both side portions. As an alternative, engaging parts may be arranged throughout the width direction (WD). As another alternative, engaging parts may be provided throughout in the width direction (WD) of the cover member 15C. As still another alternative, engaging parts may be arranged throughout the whole of the cover member 15C.

2-3. Fourth Embodiment

A sanitary napkin 1D in the fourth embodiment of the present invention is described with reference to FIGS. 17 and 18. As illustrated in FIGS. 17 and 18, the sanitary napkin 1D is different from the first embodiment in the location of the belt-shaped member 10.

Referring to FIG. 18A, in the sanitary napkin 1D of the fourth embodiment, a belt-shaped member 10 is disposed between an absorber part 4 and a back sheet part 3. A top sheet part 2 and the back sheet part 3 are connected to each other at both side portions of the sanitary napkin 1D and at the front end portion in the front region (F). With this arrangement, the belt-shaped member 10 can be extended from an opening that is an unconnected portion in the rear region (R) of the sanitary napkin 1D.

Referring to FIG. 18B, the belt-shaped member 10 may be disposed between the top sheet part 2 and the absorber part 4. In this case, a tissue 72 may be disposed between the top sheet part 2 and the absorber part 4, and the belt-shaped member 10 may be disposed between the tissue 72 and the absorber part 4. Preferably, the base material sheets 11 and 13 of the belt-shaped member 10 are hydrophilic and liquid permeable. This enables mobility of excrement such as menstrual blood from the top sheet part 2 to the absorber part 4 to be attained effectively. The top sheet part 2 and the back sheet part 3 are connected to each other at both side portions of the sanitary napkin 1D and at the front end portion in the front region (F). With this arrangement, the belt-shaped member 10 can be extended from the opening that is the unconnected portion in the rear region (R) of the sanitary napkin 1D. Alternatively, the belt-shaped member 10 may be disposed between the top sheet part 2 and the tissue 72. When an absorber part (not shown) consists of a plurality of layers, the belt-shaped member 10 may be disposed between the layers of the absorber part.

2-4. Fifth Embodiment

A sanitary napkin 1E in the fifth embodiment of the present invention is described with reference to FIGS. 19A and 19B. As illustrated in FIGS. 19A and 19B, the sanitary napkin 1E is different from the first embodiment in the direction of elongation of the belt-shaped member 10. Specifically, in the sanitary napkin 1E, the belt-shaped member 10 stretches in the direction of the front region (F).

In this case, there are the following manners of use. In a first example, after the underwear 50 is pulled down to the vicinity of the wearer's knees, the engaging part 9r in the rear region (R) of a sanitary napkin body 5E is engaged and fixed to the underwear 50. Subsequently, the engaging part 9r is pressed with one hand, the grip part 6 is gripped with the other hand, and the belt-shaped member 10 is stretched to the front region (F). The engaging part 9f is then engaged and fixed to a predetermined position of the underwear 50. Upon the completion of the attachment of the sanitary napkin 1E to the underwear 50, the underwear 50 is put on.

In a second example, after the underwear 50 is pulled down to the vicinity of the wearer's knees, the engaging part 9r in the rear region (R) of a sanitary napkin body 5E is engaged and fixed to the underwear 50. In this state, the underwear 50 is put on. Next, from the front region (F), a hand is put between the underwear 50 and the human body, and the grip part 6 is gripped and the belt-shaped member 10 is pulled to the front region (F) in order to fix the engaging material of the engaging part 9f to the underwear 50. Thus, in the sanitary napkin 1E, the belt-shaped member 10 may stretch to the front region (F).

2-5. Sixth Embodiment

A sanitary napkin 1F in the sixth embodiment of the present invention is described with reference to FIG. 20. As shown in FIG. 20, the sanitary napkin 1F in the sixth embodiment is different from the first embodiment in the direction of elongation of a belt-shaped member 10F. Specifically, the sanitary napkin 1F is formed so that the belt-shaped member 10F is stretchable to the front region (F) and the rear region (R).

A sanitary napkin body 5F and the belt-shaped member 10F are connected to each other at a connecting part 8 disposed at a substantially central region in the longitudinal direction (LD). More specifically, the sanitary napkin body 5F and the belt-shaped member 10F are connected to each other at the substantially central region of the sanitary napkin body 5F where the wearer's excretory part is brought into contact with a liquid permeable region 21 of the sanitary napkin body 5F. The belt-shaped member 10F is arranged along the longitudinal direction (LD) of the sanitary napkin body 5F, and extends toward the front region (F) and the rear region (R), respectively, with the connecting part 8 as the starting point. The term "central region" indicates a region corresponding to the wearer's excretory part, including the vaginal opening, when the sanitary napkin 1F is put on.

Both end portions in the longitudinal direction (LD) of the belt-shaped member 10F extend from the outer edge portion of both end portions of the sanitary napkin body 5F in the longitudinal direction (LD). Grip parts 6f and 6r are provided at extended portions, respectively. The non-skin contact surfaces of the grip parts 6f and 6r are provided with engaging parts 9f and 9r, respectively, which engage with the underwear 50 as an object to be engaged. The engaging parts 9f and 9r are covered with a peelable sheet 200, and are encased by a cover member 15F in this state. Since the peelable sheet 200 is connected to the cover member 15F through fixing parts 201 provided at both ends of the cover member 15F, respectively, the peelable sheet 200 can be peeled, and the engaging parts 9f and 9r can also be exposed by pulling the belt-shaped member 10F.

Therefore, in the sanitary napkin 1F, the belt-shaped member 10F is arranged along the longitudinal direction (LD) of the sanitary napkin body 5F, and both end portions of the belt-shaped member 10F are respectively fixed or engaged to a predetermined position of an engaged body such as the underwear 50. With this arrangement, the whole of the sanitary napkin body 5F can be lifted to the human body. This improves the contact between the wearer's excretory part, etc.

and the sanitary napkin 1F, thereby preventing the leakage of excrement such as menstrual blood.

The cover member 15F is required to be capable of covering at least the engaging parts 9f and 9r of the belt-shaped member 10F, which are in a non-extended state. Alternatively, the cover member 15F may be provided at a plurality of positions.

2-6. Seventh to the tenth embodiments

Sanitary napkins 1G, 1H, 1I, and 1J in the seventh to the tenth embodiments of the present invention are described with reference to FIGS. 21 to 24, respectively. As illustrated in FIGS. 21 to 24, the sanitary napkins 1G, 1H, 1I, and 1J are different from the first embodiment in having guide elements, respectively. Specifically, in the sanitary napkins 1G and 1H in the seventh and eighth embodiments, the grip parts 6G and 6H may be provided with the guide elements 73a and 73b, which indicate the directions of extension of belt-shaped members 10G and 10H, respectively. The sanitary napkins 1I and 1J in the ninth and tenth embodiments include guide elements implying a liquid permeable region 21 of the sanitary napkins 1I and 1J, respectively.

The guide elements can be attained by indication sign sheets such as arrows, symbols, illustrations, characters, colors, or color gradation, or attained by touch sense of embossing or the like. Alternatively, the guide elements may be formed with the pattern treatment of a hot melt adhesive to the skin-contact surface or the non-skin contact surface of the grip parts 6G and 6H, respectively. When the guide elements are formed by color pattern treatment of a hot melt adhesive, the base material sheets 11 and 13 in the grip parts 6G and 6H can be stuck to each other simultaneously. As an alternative, an indication sign sheet with a guide sign or the like printed thereon may be sandwiched between the base material sheets 11 and 13. As another alternative, a guide sign or the like may be directly printed on the base material sheets 11 and 13.

In the seventh embodiment, the grip part 6G extends from the outer edge portion in the rear region (R) of the sanitary napkin body 5G in the longitudinal direction (LD), and the skin-contact surface of the grip part 6G is exposed. Hence, for example, the wearer can easily find the grip part 6G, thereby increasing ease of operability. As an alternative, the grip part 6G may have a different color from the surroundings of the belt-shaped member 10G. As another alternative, for example, a symbol, an illustration, or a character may be used. As a still another alternative, the grip part 6G may be in the shape of a triangle, a circle, an ellipse, or corrugation.

In the eighth embodiment, as illustrated in FIGS. 22A and 22B, the grip part 6H may have a guide element for implying the position of the engaging part 9r to be engaged with the underwear 50. FIG. 22B illustrates the sanitary napkin 1H in which a colored sheet is arranged on the surface where a engaging material is disposed at the engaging part 9r to be engaged with the underwear 50. The guide element for implying the position of the engaging part 9r may be a colored sheet, as well as embossing, printing, colored hot melt adhesive, or the like. Alternatively, the base material sheets 11 and 13 of the belt-shaped member 10H may be formed of a sheet of high transparency so that the engaging part 9r disposed on the back sheet part 3 is made visible.

In the ninth embodiment, as illustrated in FIGS. 23A and 23B, for example, wings W1 and W2 may be disposed on both side portions of the sanitary napkin 1I, in order to imply that the liquid permeable region 21 exists at the substantially central part in the width direction of the wings W1 and W2.

In the tenth embodiment, as illustrated in FIG. 24, for example, guide elements 70 having a different color may be disposed at a predetermined position on both side portions of the sanitary napkin 1J, respectively, in order to imply that the liquid permeable region 21 exists at the substantially central part in the width direction of the guide elements 70.

As a means for implying the liquid permeable region 21, not only the position corresponding to the wearer's excretory part, but also the positions in front of and behind thereof may be specified. The guide elements 70 may be formed by embossing, colored hot melt, printing, or the like. Alternatively, a different color from the surroundings, as well as color gradation, a symbol, an illustration, a character, or a graphic symbol, may be used to imply a desired region.

2-7. Eleven Embodiment

A sanitary napkin 1K in the eleventh embodiment of the present invention is described with reference to FIG. 25. As illustrated in FIG. 25, the sanitary napkin 1K is different from the first embodiment in the arrangement of the belt-shaped member 10. Specifically, in the sanitary napkin 1K of the eleventh embodiment, a pair of belt-shaped members 10K and 10K extending in the longitudinal direction (LD) is arranged in a sanitary napkin body 5K in the width direction (WD). Alternatively, a plurality of the belt-shaped members 10K may be provided.

Thus, the pair of the belt-shaped members 10K and 10K is arranged on the non-skin contact surface of the sanitary napkin body 5K, and connected to the back sheet part 3 at connecting parts 8a and 8b disposed in the rear region (R) of the sanitary napkin body 5K. This enables, for example, the respective belt-shaped members 10K and 10K to smoothly follow the buttocks, which move independently during walking.

2-8. Others

As an alternative other than the aforementioned embodiments, the belt-shaped member may be used as an auxiliary pad by applying it to the skin-contact surface of another sanitary napkin body. In this case, the belt-shaped member is preferably smaller in the length in the width direction and in the longitudinal direction of the sanitary napkin body in order to be used together. As another alternative, the auxiliary pad formed of the belt-shaped member may be entirely formed of a liquid permeable material, or a liquid impermeable material partially having liquid-communication pores, in order to facilitate the movement of menstrual blood from the auxiliary pad to the sanitary napkin body.

3. Materials Constituting Sanitary Napkin

3-1. Sanitary Napkin Body

3-1-1. Top Sheet Part

The top sheet part 2 is, at the time of use, disposed on the human body side, and is also brought into contact with the excretory part. The top sheet part 2 may be entirely or partly liquid permeable, and it may be made of a sheet member or a plurality of sheet members adhered to each other.

As the top sheet part 2, a woven fabric, a non-woven fabric, or a sheet material having liquid permeability such as porous plastic sheet can be used. Examples of the woven fabric or the non-woven fabric are natural fibers and chemical fibers. Specifically, as the natural fiber, there are, for example, celluloses such as pulverized pulp and cotton. As the chemical fiber, there are, for example, regenerated celluloses such as rayon and fibril rayon, semi-synthetic celluloses such as acetate and triacetate, thermoplastic hydrophobic chemical fiber, and thermoplastic hydrophobic chemical fiber subjected to hydrophilization. Examples of the thermoplastic hydrophobic chemical fiber are single fibers such as polyethylene (PE), polypropylene (PP), polyethylene terephthalate (PET), fiber obtained by grafting copolymerization of polyethylene (PE) and polypropylene (PP), and composite fibers such as those having a sheath-core structure.

When the non-woven fabric is used, dry or wet web foaming such as a carding process, spun bond process, melt blown process, and air-laid process can be used. The web foaming may be a combination of the dry and wet types. As a method of bonding, there are thermal bonding, needle punch, chemical boding, and the like, without limiting to these methods. Alternatively, spun lace formed in the shape of a sheet by a spun lace process may be used.

As the porous plastic sheet, there are, for example, a porous sheet made of polyethylene (PE), polypropylene (PP), or polyethylene terephthalate (PET), and a porous foaming member.

Preferably, the porous plastic sheet is used in a clouded state by adding filler, such as titanium oxide or calcium carbonate, in the concentration range of 0.5 to 10%. Alternatively, a film may be obtained by generating pores in a thermoplastic resin film by perforation, heat embossing finish, or cutting. The porous film may be combined with the non-woven fabric to form a composite sheet.

3-1-2. Absorber Part

It is required that the absorber part 4 be able to retain and absorb excrement such as menstrual blood. Preferably, it will be difficult for the absorber part 4 to become bulky and lose its shape, and have low chemical stimulation. There are, for example, celluloses such as pulverized pulp and cotton, regenerated celluloses such as rayon and fibril rayon, semi-synthetic celluloses such as acetate and triacetate, particulate polymer, fibrous polymer, thermoplastic hydrophobic chemical fiber, thermoplastic hydrophobic chemical fiber subjected to hydrophilization, and air-laid pulp subjected to a chemical bond process. These can be used singly or mixed together.

Although no special limitation is imposed on the method of forming these materials in the absorber part 4, an air-laid process, melt blown process, spun lace process, or paper making process can be used for sheet forming.

As the absorber part 4, cellulose foam or continuous foam of synthetic resin can also be used. Alternatively, foam or the sheet-shaped material may be pulverized and then formed in an absorber.

Among others, a preferred sheet-shaped absorber has a fiber areal weight of 100 to 2000 g/m$^2$, and a thickness of 1 to 50 mm, which can be obtained by mixing pulp in the range of 80 to 100%, and particulate polymer in the range of 20% or less, then coating with tissue, followed by an embossing finish. The embossing finish is for preventing the absorber from losing its shape. The embossing area rate is preferably in the range of 10 to 100%, and more preferably 30 to 80%.

Other examples of the material of the absorber part 4 are an absorption sheet and a polymer sheet, each preferably having a thickness of 0.3 to 5.0 mm. As the absorption sheet and the polymer sheet, absorbent articles of sanitary napkins and the like may be used.

As the absorption sheet, there are, for example, an absorption paper, a non-woven fiber, and a pulp sheet obtained by forming fiber in a sheet with a binder. Examples of the polymer sheet are a pulverized pulp and a sheet obtained by mixing a particulate polymer in a fiber, and forming the mixture in a sheet. In the sheet thus obtained, the particulate polymer may be dispersed in the shape of a layer or in a three dimensional form.

The material forming the absorption sheet and the fiber used in the polymer sheet are preferably any one of cellulose fibers such as wood pulp, regenerated celluloses such as rayon and cupra, hydrophilic synthetic fibers such as a polyvinyl alcohol fiber and a polyacrylonitrile fiber, as well as polyethylene, polypropylene, polyethylene terephthalate, a polyethylene/polypropylene composite fiber, and a polyethylene/polyethylene terephthalate composite fiber, having a fiber surface hydrophilized by a surface active agent. Moreover, a cellulose fiber having hydrophilic properties is more preferable.

Preferred particulate polymers used in the polymer sheet are ones capable of absorbing and retaining 20 times its own weight in liquid, and capable of being gelatinized. There are, for example, starch, width-linked carboxymethyl cellulose, polyacrylic acid and a salt thereof, and polyacrylic acid salt graft copolymer.

3-1-3. Back Sheet Part

As the back sheet part 3, a thermoplastic film composed mainly of polyethylene (PE) or polypropylene (PP), a permeable resin film, one obtained by connecting a permeable resin film to a non-woven fiber such as spun bond or spun lace, a multilayer of SMS (spun bond/melt blown/spun bond), or the like can be used. Preferred is a film that is composed mainly of low-density polyethylene (LDPE) resin having a fiber areal weight in the range of 15 to 30 g/m². This film has flexibility and does not damage fit feeling.

When a liquid impermeable sheet is used in the belt-shaped member, the back sheet part 3 may be the same liquid permeable sheet as the top sheet part 2.

3-1-4. Connecting Part

The top sheet part 2 and the absorber part 4 can be connected by sticking them to each other with a hot melt adhesive, respectively. The top sheet part 2 and the back sheet 3 can be connected so that these are stuck to each other by a connecting part formed by a hot melt adhesive and hot pressing. As a whole, the surfaces between the adjacent sheets are adhered by the hot melt adhesive, and the ends of the sheets are connected by the connecting part formed by the hot pressing process. The connection is not limited to the hot melt adhesive. For example, a heat embossing finish and ultrasonic wave may be used singly or in combination.

As the coating pattern for when the hot melt adhesive is used for bonding, there are, for example, spiral coating, control seam coating, coater coating, curtain coating, and summit gun coating. The areal weight of the adhesive in the hot melt adhesion is preferably 1 to 30 g/m², and more preferably 3 to 10 g/m². In a pattern where adhesive is coated linearly, the diameter thereof is preferably from 30 μm to μμm.

3-2. Belt-Shaped Member

3-2-1. Base Material Sheet

As the base material sheets 11 and 13, a spun/bond non-woven fabric composed mainly of polypropylene (PP) can be used, for example. In this case, the fiber areal weight is preferably from 15 to 25 g/m². The fineness is preferably from 1.5 to 2.5 dtex.

When the back sheet part 3 is a liquid impermeable sheet, for example, each of the base material sheets 11 and 13 of the belt-shaped member 10 can employ the liquid permeable sheet as exemplified as the top sheet part 2. The base material sheets 11 and 13 are required to be a non-woven fabric having a small thickness, such as a spun bond non-woven fabric, a point bond non-woven fabric, or a spun lace non-woven fabric. This is because a non-woven fabric having a small thickness can enhance the smoothness in the expanded and contracted states of the belt-shaped member. When a concave and convex shape is applied by the corrugated embossing finish as shown in the first embodiment, it is preferable to use a spun bond non-woven fabric composed of a continuous fabric, in order to prevent the non-woven fabric from being broken during the liquid embossing finish process.

When the back sheet part 3 is a liquid permeable sheet, each of the base material sheets 11 and 13 of the belt-shaped member 10 can employ the liquid impermeable sheet as the back sheet part 3, as exemplified above. The liquid impermeable sheet may be disposed only on the skin-contact surface to the elastic member, or disposed on both the skin-contact surface and the non-skin contact surface.

3-2-2. Elastic Member

The elastic member 12 can employ, for example, an elastic yarn of natural rubber or polyurethane. Specifically, foams of an elastomer component or polyethylene foam can be used singly, or alternatively, one obtained by forming a mixture thereof in the shape of a belt or a sheet can be used. The fineness of the elastic yarn is preferably from 350 to 450 dtex. For example, the number of the elastic yarn is from seven to nine.

Examples of the elastomer component are a thermoplastic elastomer of polyester, urethane, olefin, styrene, or polyamide, low density polyethylene using metallocene catalyst, and ethylene-α-olefin copolymer. These can be used singly, or a plurality of types thereof may be blended.

As the polyester elastomer, there is, for example, one having a hard segment of aromatic polyester and soft segment of non-crystal polyether or aliphatic polyester.

As the urethane elastomer, there is, for example, a polyurethane composed of polyester, low molecular weight glycol, and methylene bisphenyl isocyanate, in which polyisocyanate is added to polylactone ester polyol and polymerized in the presence of short chain polyol.

As the olefin elastomer, there are, for example, ethylene-α-olefin random copolymer, and ethylene-α-olefin random copolymer in which diene is copolymerized as a third composition.

As the styrene elastomer, there are, for example, block copolymers such as SEBS, SIS, SEPS, and SBS.

As the polyamide elastomer, there is, for example, polyamide elastomer having a hard segment of nylon and a soft segment of polyester or polyol.

In order to stabilize the formation of the elastic member, the constitutive polymer of the elastomer composition may contain, for example, high density polyethylene, low density polyethylene, or linear low density polyethylene. It may further contain a blocking inhibitor, ultraviolet absorbing agent, thickening and branching agent, flatting agent, coloring agent, and other various improvers. Among others, the polyurethane elastic yarn is preferred due to heat or strain having less of an influence.

3-2-3. Absorber Part

When an absorber part 100 is disposed between the base material sheets 11 and 13 of the belt-shaped member 10, the same material as the absorber part 4 in the sanitary napkin body 5 can be used as the constitutive material of the absorber part 100.

When a material having absorptivity is used in the base material sheets 11 and 13 of the belt-shaped member 10, it is possible, for example, to use any woven fibers and non-woven fibers which are sheet-shaped materials, and natural fibers or chemical fibers. Examples of the natural fiber are celluloses such as pulverized pulp and cotton. Examples of the chemical fiber are regenerated celluloses such as rayon and fibril rayon, semi-synthetic celluloses such as acetate and triacetate, thermoplastic hydrophobic chemical fiber, and thermoplastic hydrophobic chemical fiber subjected to hydrophilization.

When the non-woven fabric is used, web foaming of dry type (carding process, spun bond process, melt blown process, air-laid process, or the like) or of wet type may be performed. Alternatively, these may be combined. For example, as a method of bonding, there are thermal bonding, needle punch, chemical bonding, and the like, without limiting to these methods. Alternatively, a spun lace formed in the shape of a sheet by spun lace process may be used.

3-2-4. Connecting Material

As the connecting material in connection between the base material sheets 11 and 13 and the elastic member 12, or between the base material sheets 11 and 13, a heat embossing finish, ultrasonic wave, or hot melt type adhesive can be used singly, or in combination. For example, by way of a coating method such as spiral coating, coater coating, curtain coater coating, or summit gun coating, a hot melt adhesive is applied to the base material sheet 11, and the elastic material 12 is laid thereon, followed by the base material sheet 13 being laid thereon and bonded together. In order to prevent the elastic member 12 from separating from the base material sheets 11 and 13, the elastic member 12 may be coated in advance by a coating method such as slit coating or control seam coating.

As the hot melt adhesive, there are, for example, pressure sensitive adhesives and thermo-sensitive adhesives, each composed mainly of rubbers such as SEBS, SBS, and SIS, or olefins such as linear low-density polyethylene; and water-sensitive adhesives of polyvinyl alcohol, carboxyl methyl cellulose, or gelatin, each being composed of water soluble high polymer or of polyvinyl acetate or polyacrylic acid sodium, each being composed of a water swelling high polymer. For example, it is preferable to use a heat sensitive adhesive that, even if the aforementioned adhesive effuses, has no tackiness at that point. Specifically, there are, for example, melt-mixtures of 5 to 25% of SEBS, 40 to 60% of alicyclic saturated hydrocarbon, 1 to 10% of aromatic denaturated terpene, and 15 to 35% of additive.

3-2-5. Engaging Material

A hot melt adhesive, for example, can be used as the engaging material at the engaging part 9 for engaging the sanitary napkin body and the underwear 50. Preferably, the hot melt adhesive has inherent tackiness, such as a pressure-sensitive adhesive. The main component of this adhesive is the same as in the abovementioned connecting material. Specifically, there are, for example, melt-mixtures of 15 to 25% of SEBS, 15 to 35% of plasticizer, and 40 to 70% of an adhesive-imparting agent. Furthermore, an oxidation inhibitor and fluorescence inhibitor may be added in the range of 0.1 to 1.0%. The areal weight is from 10 to 200 $g/m^2$, and coated uniformly or in a pattern of stripe-shape or dot-shape by coater coating or bead coating. As an alternative, acrylic adhesive may be used. As another alternative, the engagement may be attained by using a plurality of hook parts that stand on the surface of each tape-shaped part.

Specifically, the tape-shaped part can be formed by extrusion molding of a thermoplastic synthetic resin such as polypropylene, followed by cutting and removal of a rib structure part integrally formed with the tape part. As a result, a hook part can be formed on the surface of the tape-shaped part. As an alternative, a hook part may be formed by cutting from a side a monofilament loop composed of thermoplastic synthetic resin, which is provided on the surface of the tape-shaped part. As another alternative, the end face of the hook part may be rounded in order to eliminate the danger of damaging the skin. Specifically, the top of the hook can be rounded with the shape of a die. No special limitation is imposed on the width-sectional shape of the hook part, and it may be tapered or of T-shape.

On the other hand, as the engaging part 9 to be fixed to the wearer's body and not to the underwear 50 when the engaging part 9 is provided on the skin-contact surface of the belt-shaped member 10, there are, for example, a water-soluble polymer, width-linking agent, plasticizer, gel adhesive composed of water, and the like. Examples of the water-soluble polymer are gelatin, polyacrylic acid sodium, polyvinyl alcohol, and carboxyl methyl cellulose. Examples of the width-linking agent are water-soluble metallic salts such as calcium chloride and magnesium sulfate. Examples of the plasticizer are glycerine, wax, and paraffin.

With respect to the pressure-sensitive adhesive and the engaging part 9, the part having tackiness is preferably covered with a sheet in which a silicon resin is coated on tissue paper as generally available peelable paper, or a sheet in which silicon resin is coated on a film. This is because the adhesive part can be protected against dirt or release during storage.

3-2-6. Peelable Sheet

As the peelable sheet 200, it is possible to use a sheet obtained by coating silicon resin to a surface of a thin paper usable as a peelable sheet, or a sheet obtained by coating silicon resin on a film.

What is claimed is:

1. An elongated absorbent article, comprising:
   an absorbent article body having at least:
   (a) a top sheet part which is at least partially liquid permeable and arranged on a first side in a thickness direction of the absorbent article body,
   (b) a liquid impermeable back sheet part arranged on a second side in the thickness direction of the absorbent article body, and
   (c) a liquid retainable absorber part directly disposed between the top sheet part and the back sheet part;
   a cover member arranged on the second side in the thickness direction of the absorbent article body, wherein the backsheet part is sandwiched between the cover member and the absorber part;
   an extensible belt-shaped member disposed between the absorbent article body and the cover member, wherein said belt-shaped member has opposite first and second end portions, the first end portion of the belt-shaped member being connected to the absorbent article body, and the belt-shaped member includes belt-shaped base material sheets and an elastic member disposed between the belt-shaped base material sheets along a direction of elongation of the belt-shaped member;

an engaging part arranged at the second end portion of the belt-shaped member and on a surface of the belt-shaped member on which the cover member is disposed;

a peelable sheet releasably engageable with and arranged along a surface of the engaging part; and a fixing part fixing the peelable sheet to the cover member, the fixing part being formed so that an end portion thereof in the direction of elongation of the belt-shaped member is arranged at a first position corresponding to an end portion of the engaging part in the direction of elongation, or a second position further away from the end portion of the engaging part in the direction of elongation.

2. The absorbent article according to claim 1, wherein the cover member is arranged so as to encase at least a part of the engaging part.

3. The absorbent article according to claim 1, wherein at least a part of the belt-shaped member is flexible.

4. The absorbent article according to claim 1, wherein the belt-shaped member has a grip part at the second end portion thereof, the grip part projecting beyond an outer edge of the absorbent article body in the direction of elongation.

5. The absorbent article according to claim 4, wherein the grip part has a guide element indicating the direction of elongation of the belt-shaped member.

6. The absorbent article according to claim 4, wherein the second end portion of the belt-shaped member is provided with an absorbent member.

7. The absorbent article according to claim 6, wherein the absorbent member is arranged beyond the outer edge of the absorbent article body in the direction of elongation when the belt-shaped member is in one of an extended state and a stretched state.

8. The absorbent article according to claim 6, wherein the belt-shaped member has a liquid impermeable sheet disposed corresponding to the absorbent member on the opposite side of the absorbent article body.

9. The absorbent article according to claim 1, wherein a width of the belt-shaped member in a width direction perpendicular to the direction of elongation is at least 30% of a width of the absorbent article body in the width direction.

10. The absorbent article according to claim 1, wherein at least a part of the belt-shaped member has a liquid impermeable material.

11. The absorbent article according to claim 1, wherein at least a part of the cover member is formed of a liquid impermeable material.

12. The absorbent article according to claim 1, wherein at least a part of the cover member is formed so as to be stretchable in a width direction perpendicular to the direction of elongation of the belt-shaped member.

13. The absorbent article according to claim 1, wherein said cover member has at least a part attached to the back sheet.

14. The absorbent article according to claim 4, wherein said peelable sheet is releasably attached to the surface of the engaging part without projecting beyond the outer edge of the absorbent article body in the direction of elongation.

15. The absorbent article according to claim 1, wherein the fixing part is directly disposed on the cover member.

* * * * *